United States Patent
Dutta et al.

(10) Patent No.: US 9,217,721 B2
(45) Date of Patent: Dec. 22, 2015

(54) NO SENSOR AND SENSOR SYSTEMS

(71) Applicant: The Ohio State University, Columbus, OH (US)

(72) Inventors: Prabir Dutta, Worthington, OH (US); Chenhu Sun, Columbus, OH (US); Maduraiveeran Govindhan, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 364 days.

(21) Appl. No.: 13/780,437

(22) Filed: Feb. 28, 2013

(65) Prior Publication Data
US 2013/0219988 A1 Aug. 29, 2013

Related U.S. Application Data

(60) Provisional application No. 61/604,752, filed on Feb. 29, 2012.

(51) Int. Cl.
| | |
|---|---|
| *G01N 29/02* | (2006.01) |
| *G01N 31/00* | (2006.01) |
| *G01N 33/497* | (2006.01) |
| *G01N 7/00* | (2006.01) |
| *G01N 9/00* | (2006.01) |
| *G01L 7/00* | (2006.01) |
| *G01N 27/04* | (2006.01) |
| *G01N 27/12* | (2006.01) |

(52) U.S. Cl.
CPC .............. *G01N 27/04* (2013.01); *G01N 27/129* (2013.01); *G01N 33/497* (2013.01)

(58) Field of Classification Search
None
See application file for complete search history.

(56) References Cited

U.S. PATENT DOCUMENTS

| | | | | |
|---|---|---|---|---|
| 4,949,065 | A * | 8/1990 | Watanabe et al. | 338/308 |
| 6,794,728 | B1 * | 9/2004 | Kithil | 257/532 |
| 7,205,256 | B2 * | 4/2007 | Kijima et al. | 502/232 |
| 7,217,355 | B2 * | 5/2007 | Nair et al. | 205/781 |
| 8,129,725 | B2 * | 3/2012 | Kunze et al. | 257/76 |
| 8,162,710 | B2 * | 4/2012 | Okumura | 445/25 |
| 2012/0161790 | A1 * | 6/2012 | Smith et al. | 324/658 |
| 2013/0264660 | A1 * | 10/2013 | Fleischer et al. | 257/414 |

FOREIGN PATENT DOCUMENTS

EP 1217361 A2 * 6/2002

* cited by examiner

*Primary Examiner* — Peter Macchiarolo
*Assistant Examiner* — Jermaine Jenkins
(74) *Attorney, Agent, or Firm* — Meunier Carlin & Curfman LLC

(57) ABSTRACT

Some aspects of the present disclosure relate to a sensor design that exploits the different majority carriers (holes/electrons) in $WO_3$ and $Cr_2O_3$ to build sensitivity and selectivity to NO at ppb levels, while discriminating against CO at concentrations a thousand-fold higher (ppm) and spread over a considerable range (0-20 ppm). Practical application of this sensor system for detecting NO in human breath is demonstrated.

17 Claims, 27 Drawing Sheets

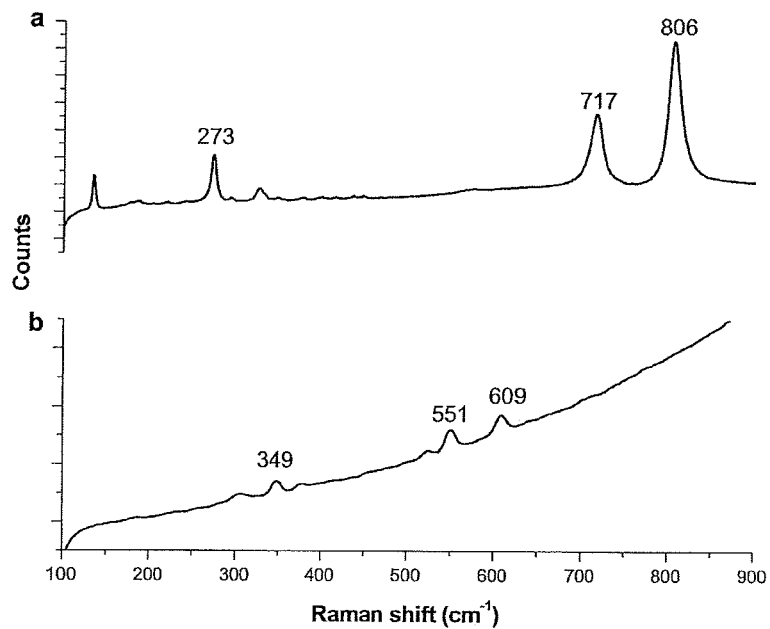
FIGURE 16A
FIGURE 16B
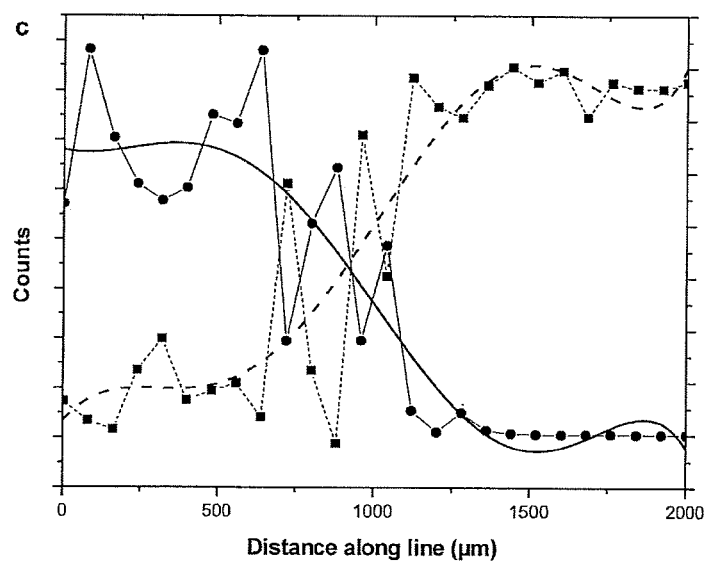
FIGURE 16C

NO SENSOR AND SENSOR SYSTEMS

CROSS-REFERENCE TO RELATED APPLICATIONS

This Non-Provisional Patent Application claims the benefit of the filing date of U.S. Provisional Patent Application Ser. No. 61/604,752, filed Feb. 29, 2012, entitled "OBTAINING SELECTIVITY IN GAS SENSORS VIA A SENSOR ARRAY SYSTEM COMPOSED OF P AND N TYPE MATERIAL," the teachings of which are herein incorporated by reference.

BACKGROUND

There is extensive research in developing selective and sensitive gas sensors for applications spanning an incredible range of technologies, from environmental, energy optimization, food, health and security. Just as the applications are varied, so are the types of gas sensing technologies that are being developed, with major advances being made in optical and electrochemical devices. There have been some remarkable successes, for example the ubiquitous electrochemical oxygen sensor for combustion control as well as fire detection sensors. The challenges in this field continue to be developing selectivity and sensitivity with respect to specific gases present in harsh environments, and reducing the foot print of the sensing device and measurement system.

A good example of an unmet sensing need is control of NO emissions for transportation systems running on diesel fuel. In the after treatment system for reducing NO emissions, NO sensors are required with discrimination against other combustion gases, and capable of operation under very harsh environments. NO sensors are also required for breath analysis for diagnosis of respiratory diseases. The most common measurement technique in breath monitoring is the chemiluminescence analyzer, however this apparatus is bulky, and requires a supply of ozone. There is considerable interest in developing minaturizable electrochemical sensors that have high sensitivity (ppb level) to NO and yet can discriminate against hundreds of other molecules in breath.

Metal oxide semiconductors (MOS)-based sensors (n-type: $SnO_2$, $ZnO_2$, $TiO_2$, $WO_3$, etc.; p-type: $CuO$, $Cr_2O_3$, etc.) may be used to detect volatile compounds (such as acetone, propanol, ethanol) or toxic gases (such as CO, NO, $NO_2$, etc.). In general terms, MOS sensors incorporate a sensing layer formed of material selected for a targeted gas. When the targeted gas interfaces with the sensing layer material, the target gas molecules are adsorbed on the crystal surface, resulting in a change in conductivity of the sensing layer. By measuring the change in conductivity (e.g., resistivity), the presence and amount (often in ppm or ppb) of the targeted gas (or other compound or analyte of interest) can be estimated. Sensitivity/selectivity to a particular gas depends on the intrinsic properties of the MOS material, and can be modulated by doping to alter the electrical properties or by introducing catalysts such as Au, Pt, Pd to alter the chemical properties.

The concept of using p and n-type semiconducting oxide (MOS) as well as their mixtures to improve sensor performance is reported in the literature. For the mixtures of p and n-type materials, there are primarily two strategies, mixing p- and n-type powders or creating a p-n diode-type junction.

For particular ratios of powder mixtures of n-type anatase and p-type rutile, it has been found that the resistance change is minimal towards CO and $CH_4$. Based on a polychromatic percolation model, it was proposed that at these particular powder mixture ratios, the two parallel conduction pathways based on n-n and p-p paths cancel each other. Other studies have noted similar effects, for mixtures of ZnO (n-type) and Al-doped CuO (p-type) increasing CuO exhibited lower response to CO. In another study, Pt loading on mixtures of n-type ZnO and p-type CuO, led to an overall p-type response towards CO. CO selectivity was also noted for CuO/ZnO heterocontacts. Other strategies have been to put p-type $Co_3O_4$ nanoparticles on n-ZnO nanowires, as well as nanocomposites and p-type CuO on n-type $SnO_2$ nanorods exhibited high sensitivity to $H_2S$.

There are several studies in the literature focused on gas sensing which report the formation p-n junctions that exhibit I-V characteristics indicative of rectification. These include n-ZnO/p-CuO, $Pt/SnO_2/n-Si/P^+$—Si/Al, p-ZnO/n-ZnO, ZnO (p-type)/n-Si heterojunctions, and $n-SnO_2/p-Co_2O_3$ (or $Cr_2O_3$).

Still other studies have demonstrated that both $WO_3$ and $Cr_2O_3$ exhibit an increase in resistance upon exposure to NO, whereas in the presence of CO, there is an increase in resistance for $Cr_2O_3$ and a decrease in resistance with $WO_3$.

In light of the above, a need exists for sensors, and related sensor systems, for sensing NO in various environments, including human breath.

SUMMARY

Some aspects of the present disclosure relate to a new sensor design that exploits the different majority carriers (holes/electrons) in $WO_3$ and $Cr_2O_3$ to build sensitivity and selectivity to NO at ppb levels, while discriminating against CO at concentrations a thousand-fold higher (ppm) and spread over a considerable range (0-20 ppm). Practical application of this sensor system for detecting NO in human breath is demonstrated. In some embodiments, NO sensor devices (and corresponding systems) of the present disclosure include a sensor element including WO3 and Cr2O3 arranged adjacent one another and forming a diffuse p-n junction. A first electrode is in contact with the WO3 region, and a second electrode is in contact with the Cr2O3 region. Wiring interconnects the first and second electrodes, with a measured resistance at the wiring being indicative of the presence of NO in a sample gas interacting with the sensing element. In this regard, a location of the first and second electrodes relative to the corresponding WO3 and Cr2O3 region, and thus a distance or length of the wiring, is selected such that the presence of CO in the sample gas has minimal, if any, effect on the measured resistance. Further, a pre-determined calibration curve (or other database such as a table) can be provided with the sensor device (e.g., software loaded to a computer or other controller) that correlates the measured resistance with NO concentration. With these optional systems of the present disclosure, a sample gas having an unknown concentration of NO (including possibly zero NO) is caused to interact with the sensor device and the resistance along the wiring is measured and compared with the predetermined calibration curve to estimate whether NO is present in the sample gas and if present, an estimate of the NO concentration.

BRIEF DESCRIPTION OF THE DRAWINGS

FIG. 16A is a graph of Raman spectra of $WO_3$ powder useful with sensor devices of the present disclosure;

FIG. 16B is a graph of Raman spectra of $Cr_2O_3$ powder useful with sensor devices of the present disclosure;

FIG. 16C is a graph illustrating integrated Raman intensities from a map of the junction of $Cr_2O_3$ and $WO_3$ materials akin to the junction of FIG. 15B;

DETAILED DESCRIPTION

Figure 1:
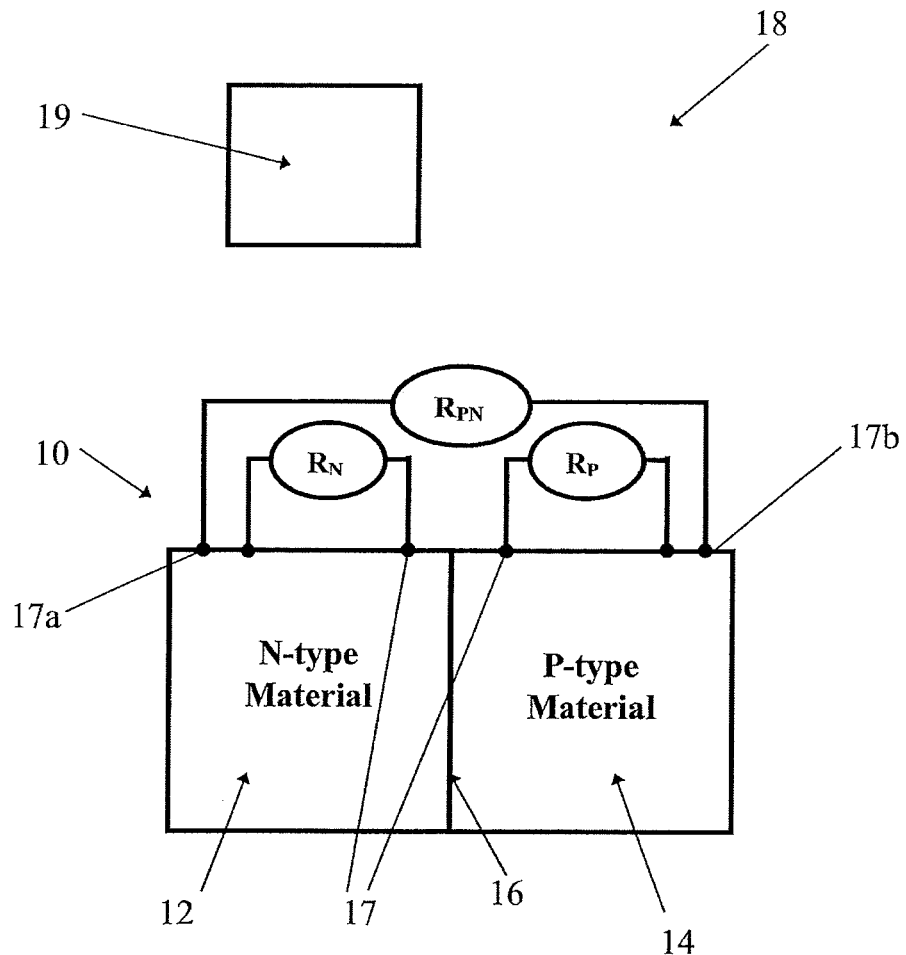
FIG. 1 is a schematic illustration of a sensor device provided as part of a sensor system in accordance with principles of the present disclosure.

In general terms, sensor devices and corresponding sensor systems of the present disclosure are configured to sense the presence and concentration of NO, including discriminating against the presence of CO. The sensor devices of the present disclosure are akin to MOS-type gas sensors, and can incorporate selected p-type and n-type materials arranged adjacent one another in forming the sensing element of the sensor device. In this regard, techniques for obtaining data from the so-constructed sensor device can assist in distinguishing NO from a mixture of gases. By way of background, FIG. 1 schematically illustrates one embodiment of a sensor device 10 in accordance with principles of the present disclosure. The sensor device 10 includes a sensing element 11 akin to a MOS sensing element, but formed by at least two discrete MOS materials. Namely, the sensing element 11 includes a first, n-type MOS material region 12 and a second, p-type MOS material region 14. A diffuse p-n junction 16 is established between the n-type region 12 and the p-type region 14. The n-type and p-type regions 12, 14 are formed immediately adjacent one another and can contact one another at the p-n junction 16. Electrodes or other electrical lead-type bodies (identified generally at 17 in FIG. 1) are, or can be, selectively or permanently established at nodes within each of the regions 12, 14 (e.g., gold electrodes provided with a gold microspring array (now shown)). Electrical connections (e.g., wires) can be established between selected pairs of the so-established electrodes or nodes 17, with FIG. 1 illustrating three possible connections as measured resistances $R_{PP}$, $R_{NN}$, and $R_{PN}$. $R_{PP}$ represents a measured resistance between two nodes 17 only in the p-type region 12. $R_{NN}$ represents a measured resistance between two nodes only within the n-type region 14. $R_{PN}$ represents a measured resistance spanning both the p- and n-type regions 12, 14 (e.g., the electrodes 17a and 17b of FIG. 1). In one embodiment, a platform (not shown) supports the sensor element 11 and can be maintained at a temperature optimized for the analyte.

The sensor device 10 can be provided as part of a sensor system 18 in accordance with principles of the present disclosure. The sensor system 18 can include components conventionally employed with MOS-type gas sensor systems, such as a housing (now shown) for directing a gas or other substance of interest across the sensing element 11, electronics for establishing and measuring conductivity at the desired connections (e.g., $R_{PP}$, $R_{NN}$, $R_{PN}$), and a controller 19 (e.g., a computer or other logic device) for receiving and/or interpreting the measured conductivity signals. In some embodiments, a measurement device (e.g., a multimeter) can be provided apart from the controller 19 that measures resistance at the selected connection(s), and signals the measured resistance value(s) to the controller 19 for interpretation as described below. The sensor system 18 can, in some embodiments, be provided as a single unit, such as a hand-held device providing an inlet port through which a gas sample is introduced. Regardless, the controller 19 is further programmed to determine the presence and amount (e.g., in ppm or ppb) of one or more analytes (e.g., ambient gas) of interest based upon the measured conductivity signals. With some particular embodiments of the present disclosure, the controller 19 is programmed to operate the sensor device 10 and analyze data generated thereby to detect the presence of, and estimate the concentration of, NO in various sample types, including human breath samples. In yet other embodiments, some or all of the measured resistance interpretation can be performed manually such that the controller 19 is optional.

The p-type material region 12 consists of a p-type MOS material that conducts with positive holes being the majority charge carrier. In the presence of an oxidizing gas, the p-type MOS material exhibits an increase in conductivity (or decrease in resistivity). An opposite effect is exhibited by the p-type MOS material in the presence of a reducing gas. While various p-type MOS materials are available, it has surprisingly been found that $Cr_2O_3$ as the p-type region 12 material (in combination with other features of the sensor device 10 described herein) is well suited for detection of NO.

The n-type material region 14 consists of an n-type MOS material in which the majority charge carriers are electrons. Upon interaction with an oxidizing gas, the n-type MOS material exhibits a decrease in conductivity (or increase in resistivity). An opposite effect is exhibited by the n-type MOS material in the presence of a reducing gas. While various n-type MOS materials are available, it has surprisingly been found that $WO_3$ as the n-type region 14 material (in combination with other features of the sensor device 10 described herein) is well suited for detection of NO.

Figure 2:
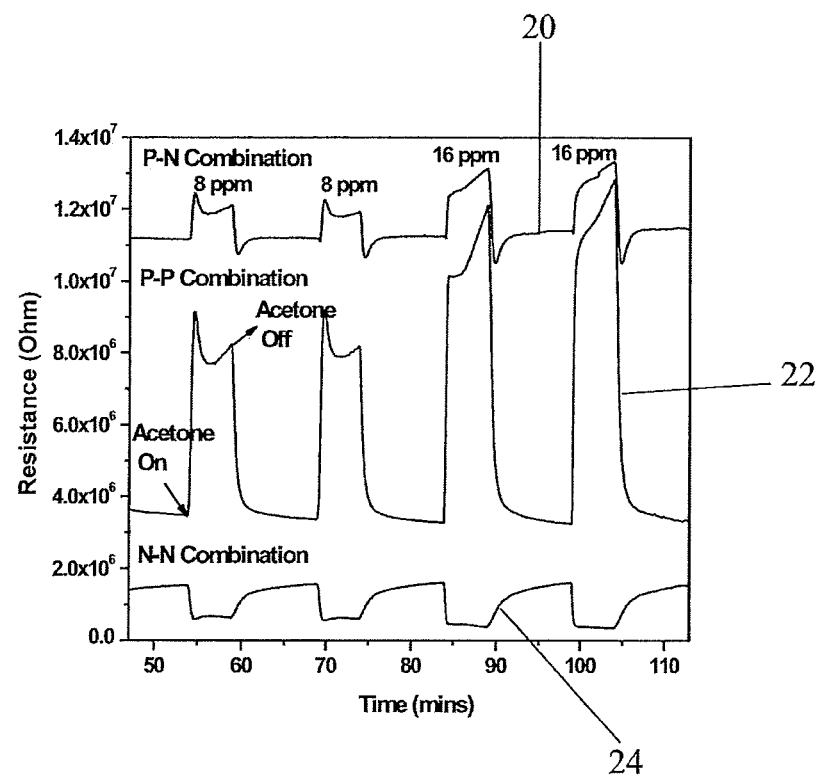
FIG. 2 is a graph illustrating sensor response to acetone of a sensor device having a p-type material of CuO and an n-type material of $SnO_2$.

The measured conductivities at the p-type region $R_{PP}$, at the n-type region $R_{NN}$, and across the p-n junction $R_{PN}$ can be evaluated to determine the presence and amount of a particular gas. As a point of reference, it has been determined that sensor devices akin to the sensor device 10 (i.e., p-type and n-type MOS materials arranged adjacent one another) can provide discriminating conductivity signals across the p-n junction 16 with materials other than, and in addition to, $Cr_2O_3$ and $WO_3$. For example, FIG. 2 illustrates response of a sensor device incorporating CuO as the p-type material region 12 and $SnO_2$ as the n-type material region 14 to 10% $O_2$ and 8 ppm or 16 ppm acetone. The measured resistance across the p-n junction 16 (i.e., $R_{PN}$) is identified at 20, at the p-type region 12 (i.e., $R_{PP}$) is identified at 22, and at the n-type region 14 (i.e., $R_{NN}$) is identified at 24. FIG. 2 demonstrates that the response 20 to acetone decreases across the p-n junction 16, as compared to the p-type response 22 in the p-type region 12.

Figure 3:
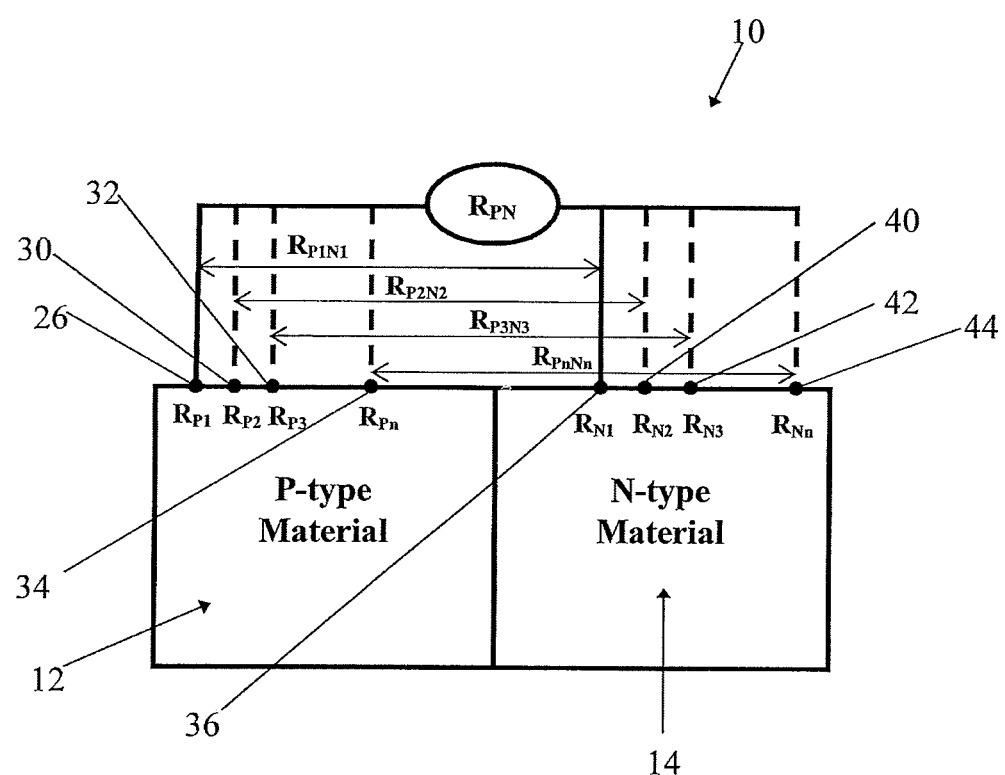
FIG. 3 is a schematic illustration of a sensor device of FIG. 1 along with electrodes in accordance with principles of the present disclosure.

The signal analysis in accordance with the present disclosure can assume various forms, and can include obtaining a multiplicity of p-n junction measurements at differing nodes within the p-type region and the n-type region. For example, FIG. 3 illustrates an alternative layout of leads or nodes (and corresponding electrical connections or wires) along the sensor device 10 and will help explain further the basis of the analyte identification based on a concept of cancellation. With a proper combination of the p-type material in the p-type region 12 and n-type material in the n-type region 14, using one of the lead wires from the electrodes or nodes at $R_{P1}$ 26, $R_{P2}$ 30, $R_{P3}$ 32, $R_{Pn}$ 34 in the p-type region 12 and other lead wires from the electrodes or nodes at $R_{N1}$ 36, $R_{N2}$ 40, $R_{N3}$ 42, $R_{Nn}$ 44 in the n-type region 14, the analyte signal may diminish completely and may be treated as null response for the particular analyte. Thus, different types of analyte molecules will have unique null response spacings. For example, a first analyte will have a null response spacing between $R_{P1}$ 26 and $R_{N1}$ 36, a second (different) analyte will have a null response spacing between $R_{P2}$ 30 and $R_{N2}$ 40, etc.

With the above in mind, the null response data can be used as a "fingerprint" signature that is unique to a specific analyte. Thus, in a blind study, systems of the present disclosure can elucidate the identity of analytes using this "fingerprint" signature technique. For example, the controller 19 (FIG. 1) can be programmed to include a database of various analytes and their corresponding, previously-determined null response data; the controller 19 can compare the conductivity information (e.g., null spacing data) for an unknown analyte being tested with the database to identify the unknown analyte.

Figure 4:
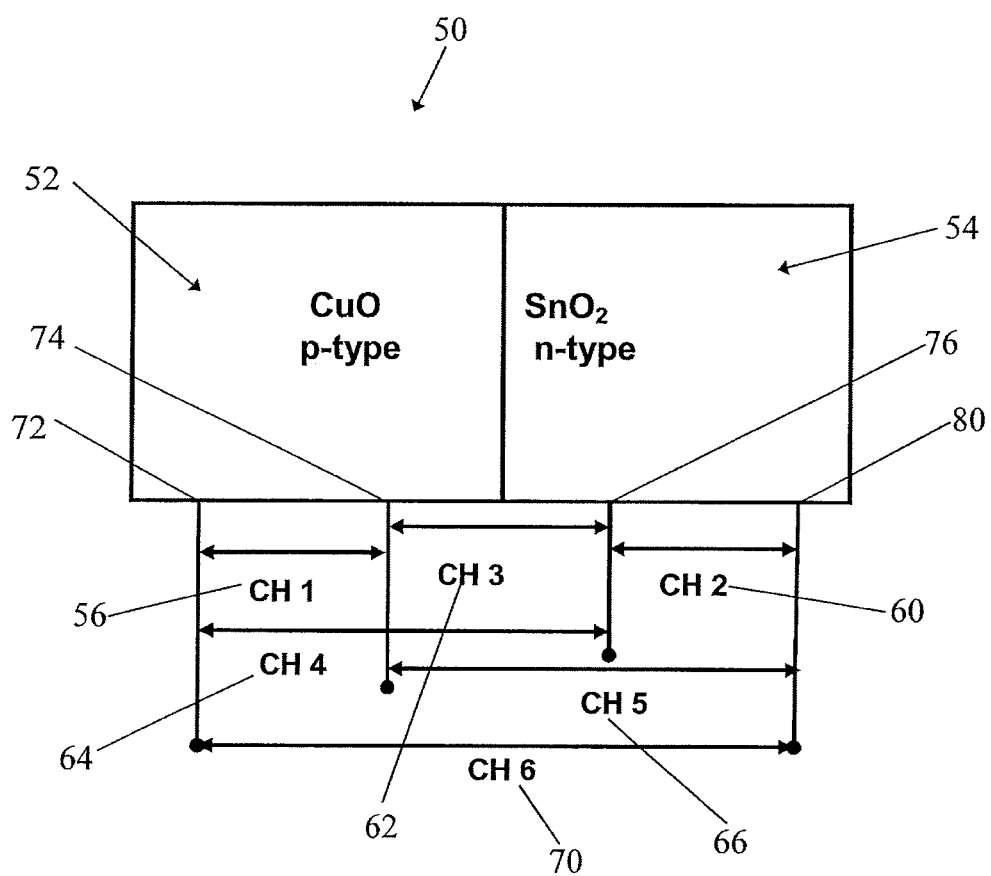
FIG. 4 is a schematic illustration of another sensor device and corresponding electrodes in accordance with principles of the present disclosure.
Figure 5:
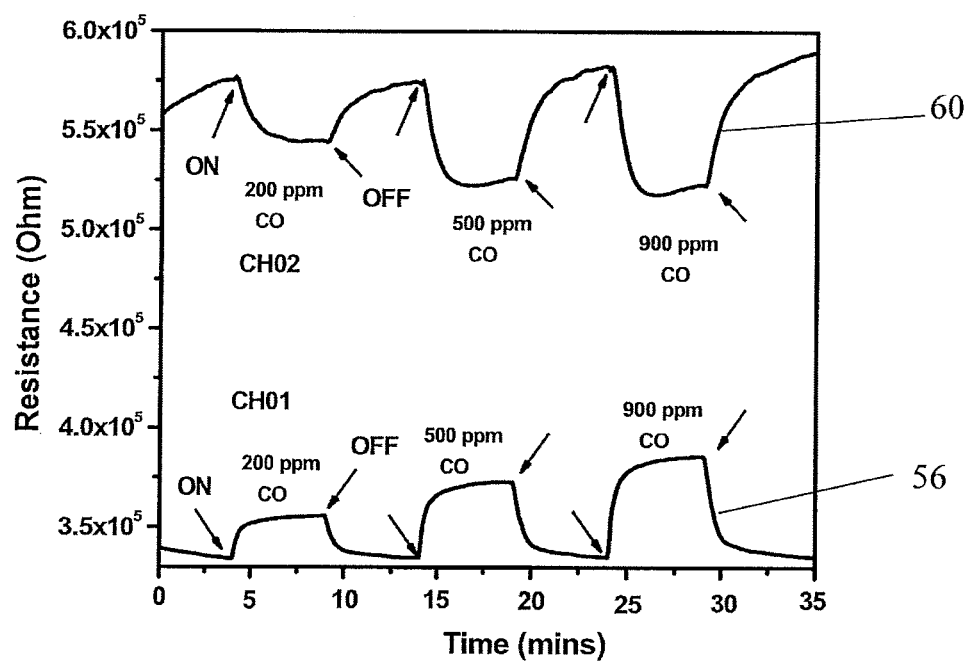
FIG. 5 is a graph illustrating response of the sensor device of FIG. 4 to the presence of CO.
Figure 6:
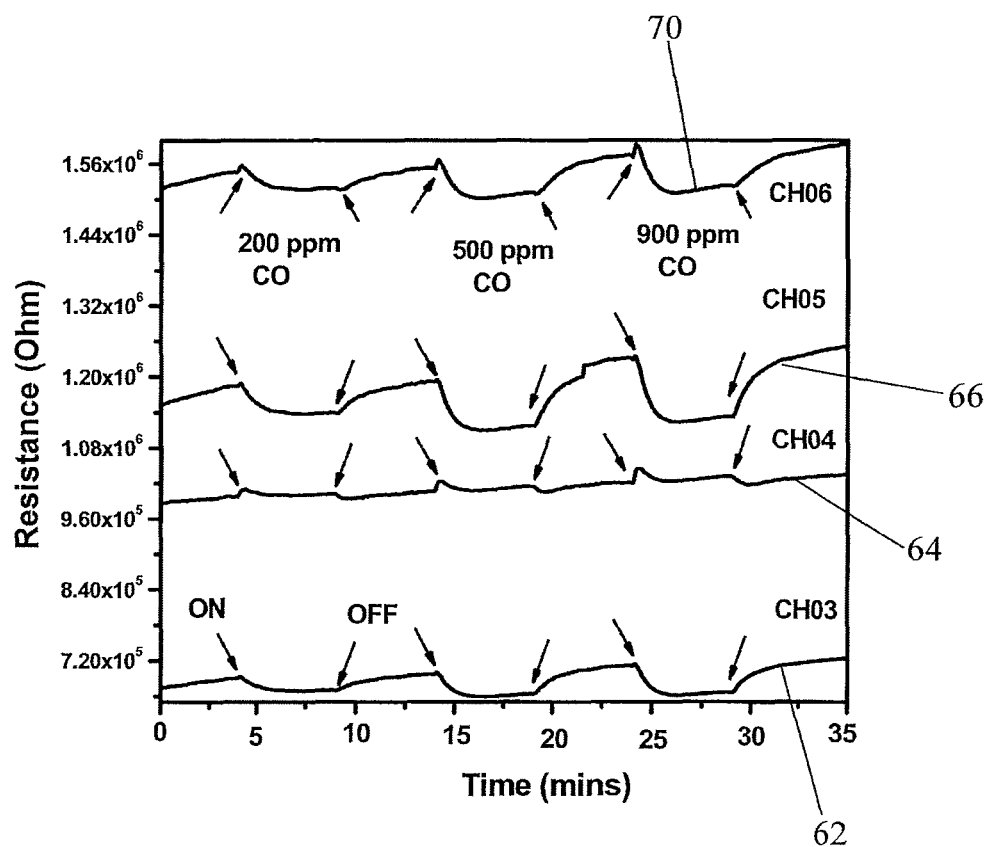
FIG. 6 is a graph illustrating response of the sensor device of FIG. 4 to the presence of CO, including a cancelation signal.

As an example for the case of CO, FIG. 4 shows another sensor device 50 which is an array of p-type CuO material 52 and n-type $SnO_2$ material 54. Channels 1-6 ("CH 1"-"CH 6") 56, 60, 62, 64, 66, 70 are illustrated between various electrodes wires from the electrodes or nodes 72, 74, 76, 80. FIG. 5 illustrates graphs of sensed resistances at Channels 1 and 2 56, 60 and FIG. 6 illustrates graphs of Channels 3, 4, 5 and 6 62, 64, 66, 70. Channel 1 56 measures resistance in the p-type region 52 and Channel 2 60 measures resistance in the n-type region 54. Channels 1 and 2 56, 60 illustrate expected resistance increases and decreases, respectively, (as measured from the ON points to the respective OFF points) in the presence of CO.

With continued reference to FIG. 6, the response to CO is nullified as illustrated by Channel 4 64. It is contemplated that the CO is nullified along Channel 4 64 because the signal through the n-type material 54 cancels the signal through the p-type material 52 over the distance between the electrode wires 72 in the p-type material 52 and the electrode 76 in the n-type material 54. Although Channel 5 (between the electrode 74 in the p-type material 52 and the electrode 80 in the n-type material 54) is approximately the same distance as Channel 4, the path of Channel 5 travels through more of the n-type material 54 relative to the path of Channel 4.

Figure 7:
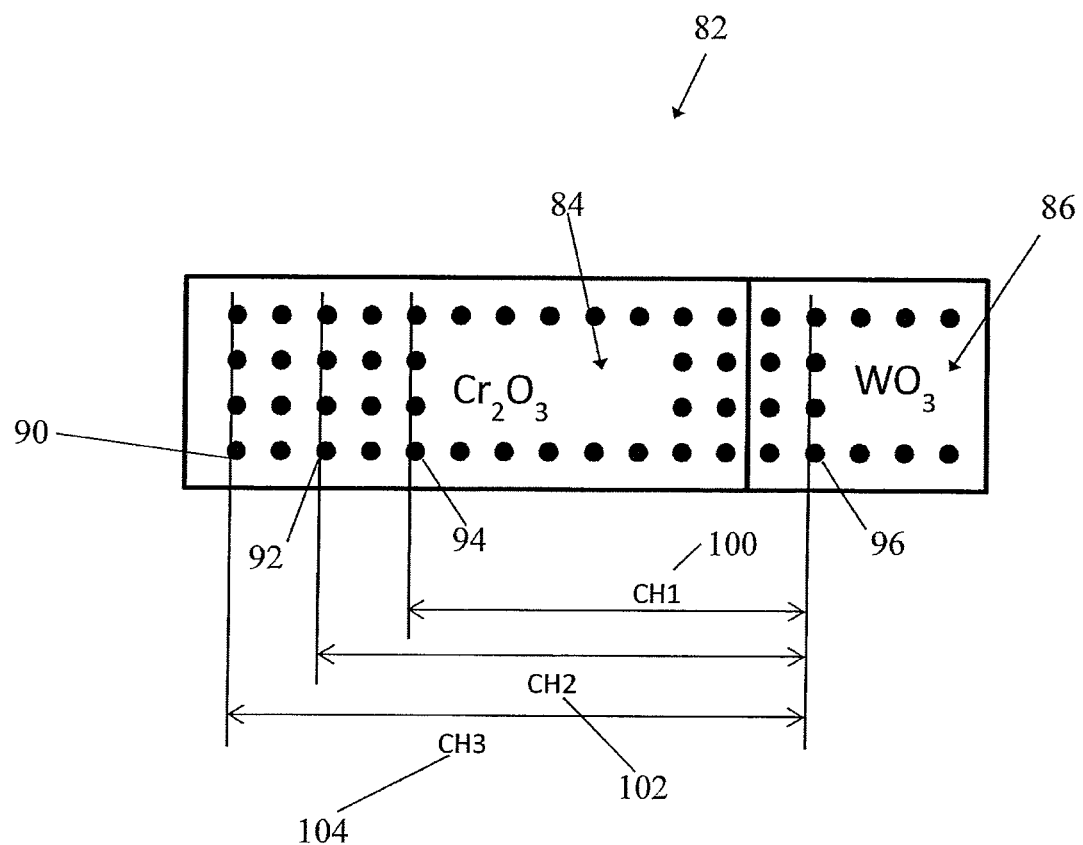
FIG. 7 is a schematic illustration of a sensor device in accordance with principles of the present disclosure including $Cr_2O_3$ and $WO_3$ materials.

With the above background in mind, NO sensors and corresponding sensor systems of the present disclosure incorporate $Cr_2O_3$ as the p-type material, and $WO_3$ as the n-type material. With reference to FIG. 7, a sensor device 82 in accordance with the present disclosure is schematically illustrated as including a p-type material 84 of $Cr_2O_3$ and n-type material 86 of $WO_3$, and is surprisingly found to have very high sensitivity to NO and discrimination against CO, even though the CO may be present at several orders of magnitude higher concentrations. Electrode wires are illustrated as extending from electrodes or nodes 90, 92, 94 in the p-type $Cr_2O_3$ material 84, and an electrode wire is illustrated as extending from an electrode or node 96 in the n-type $WO_3$ material. Channels 1, 2, and 3 ("CH 1"-"CH 3") 100, 102, 104 are illustrated between the wire of the electrode 96 and the wires of the electrodes 90, 92, 94, respectively.

Figure 8:
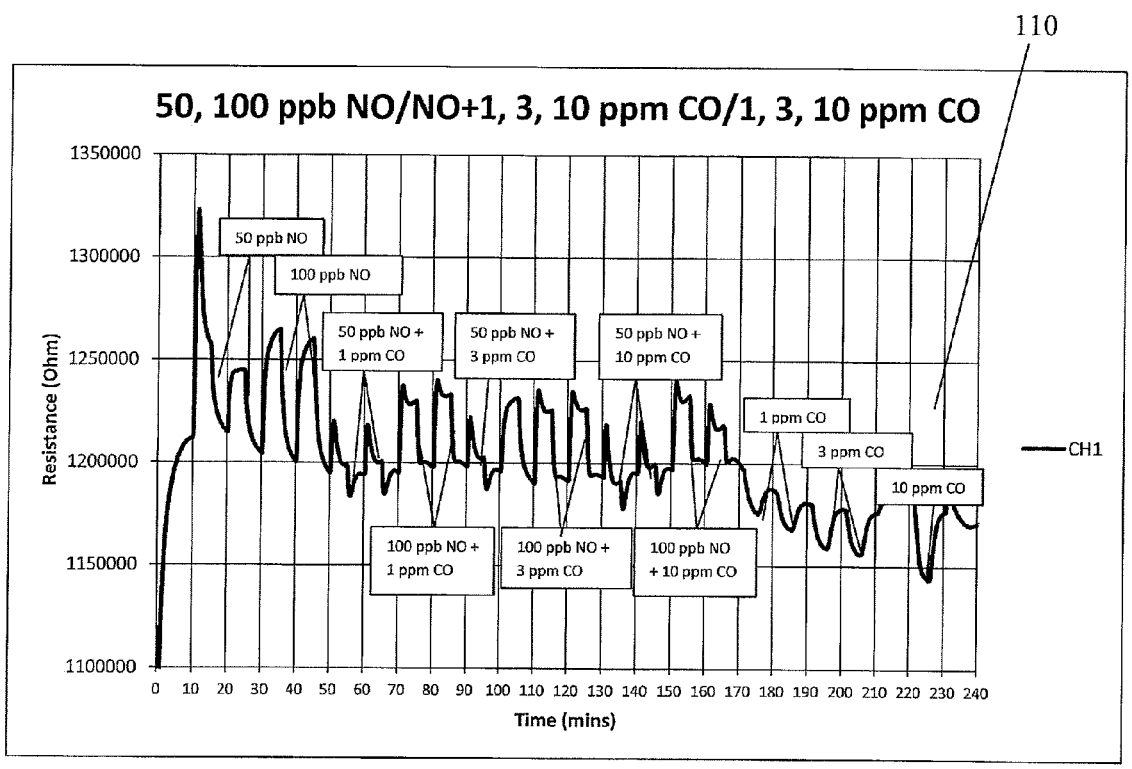
FIG. 8 is a graph illustrating response of a first channel in the sensor device of FIG. 7 to the presence of various gases.

The measured resistance at each of the channels 100-104 differs in the presence of NO or CO, and varies as a function of the NO and CO concentrations. FIG. 8 illustrates a graph 110 of the data measured resistance obtained from Channel 1 100 in response to combinations of 20% $O_2$ with various concentrations of NO and CO, including: 50 and 100 ppb NO; 50 and 100 ppb NO+1 ppm CO; 50 and 100 ppb NO+3 ppm CO; and 50 and 100 ppb NO+10 ppm CO as well as 1, 3 and 10 ppm CO. The concentrations are marked on the figure. An increase in resistance was observed at NO concentrations of both 50 and 100 ppb, whereas CO at 1, 3 and 10 ppm shows a decrease in resistance, with higher concentrations in both cases exhibiting a progressively increasing signal. With the mixture of NO and CO, the signal for 50 ppb NO is decreased and the 100 ppb signal is smaller than the signal obtained in the absence of CO.

Figure 9:
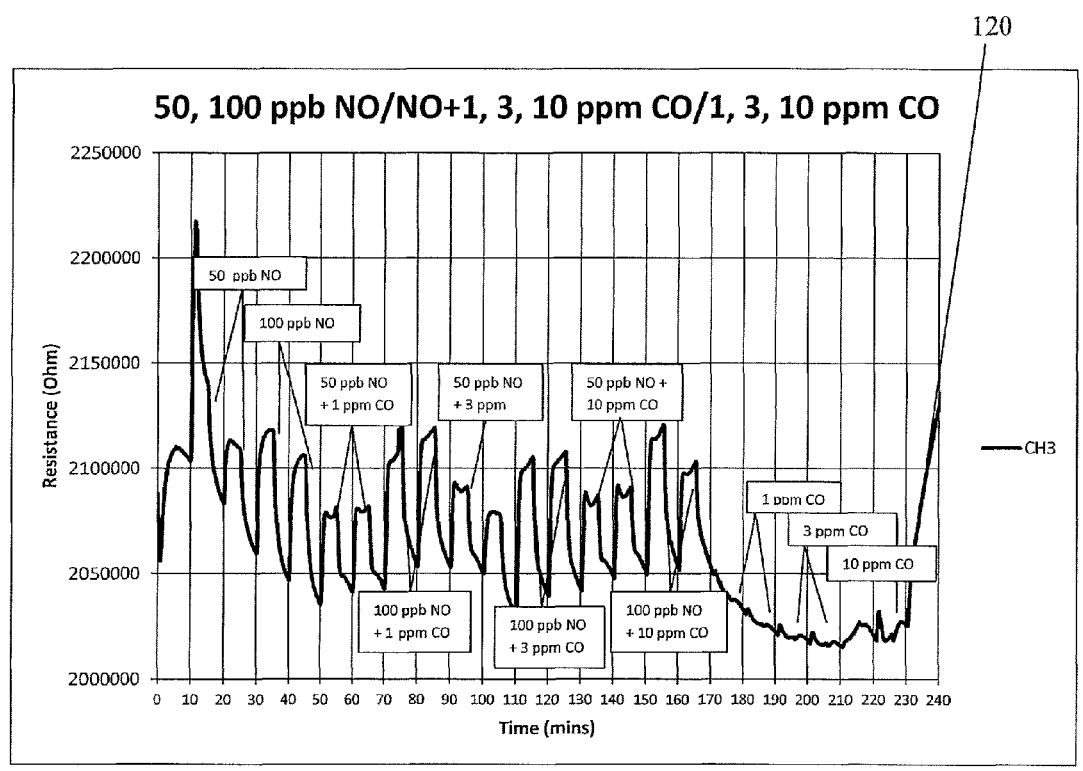
FIG. 9 is a graph illustrating response of a second channel in the sensor device of FIG. 7 to the presence of various gases.

The observations of the graph 110 of FIG. 8 may be contrasted with a graph 120 in FIG. 9 of the data obtained (for the same combination of gas mixtures) from Channel 3 104. The CO signal at 1, 3 ppm is completely nulled and a very small signal is observed for 10 ppm CO (see relatively flatter area toward the right of the graph 120 in FIG. 9). As compared to channel 1 100, the Channel 3 104 signal for NO at both 50 and 100 ppb remain constant in the presence of CO, demonstrating that the nulling effect by virtue of the n-p sensor array for a specific analyte can be exploited to improve selectivity.

Figure 10:
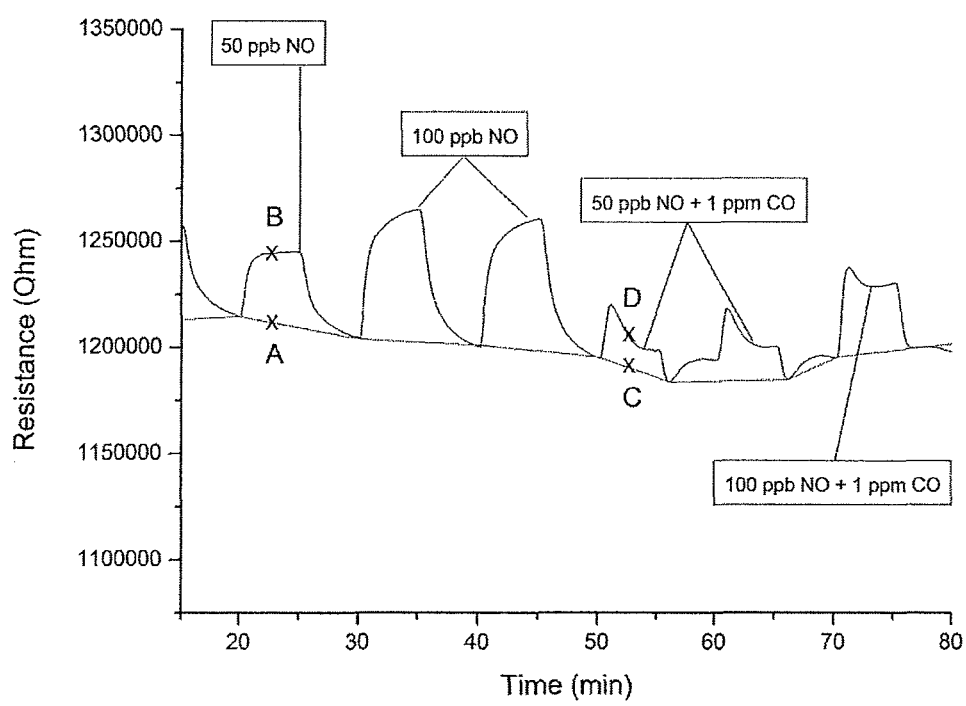
FIG. 10 is an enlarged portion of the graph of FIG. 8 between 15 minutes and 80 minutes.

With reference to the graph 110 in FIGS. 8 and 10, the resistance at about 22.5 minutes (along the x-axis) is about 1211877 ohms for a baseline (A), and the resistance at a point B due to 50 ppb NO is about 1244257 ohms, indicating a total difference of about 32380 ohms arising from the 50 ppb NO. At about 52.5 minutes (in the 50 ppb NO+1 ppm CO region), the resistance at a baseline C is about 1190603 ohms, and at a signal D (in the NO+CO region), the resistance is about 1205768 ohms, giving a total signal of about 15165 ohms. The difference between the pure NO region and the NO+CO region is about 17215 ohms.

Figure 11:
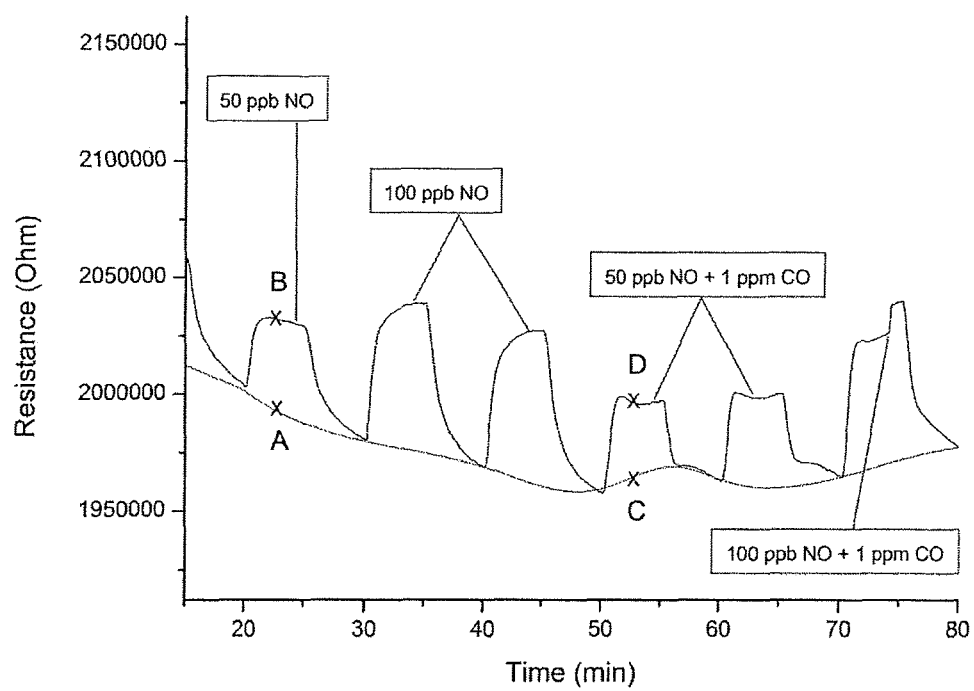
FIG. 11 is an enlarged portion of the graph of FIG. 9 between 15 minutes and 80 minutes.

With reference to the graph 120 in FIGS. 9 and 11, the resistance at about 22.5 minutes (along the x-axis) at a baseline point A is about 1993523 ohms, and the resistance due to 50 ppb is about 20319171 ohms, leading to a signal of 38448 ohms for the 50 ppb NO. The difference between 2120000 ohms and 2080000 ohms is about 40000 ohms. At about 52.5 minutes (in the 50 ppb NO+1 ppm CO region), the resistance for a baseline point C is about 1964002 ohms, and for the signal due to (50 ppb NO+1 ppm CO) at a point D, the resistance is about 1996495 ohms. The signal is about 32493 ohms. The difference between the pure NO region and the NO+CO region is about 5955 ohms.

With reference to FIGS. 8-11, the 17215 ohm difference (FIGS. 8 and 10) between the pure NO region and the NO+CO region is larger than the 5955 ohm difference (FIGS. 9 and 11) between the pure NO region and the NO+CO region. The smaller difference in FIGS. 9 and 11 (relative to FIGS. 8 and 10) between the pure NO region and the NO+CO region indicates the graph 120 in FIGS. 9 and 11 is less affected by CO than the graph 110 in FIGS. 9 and 10. Therefore, Channel 3 104 (see FIG. 7) between the electrode 90 (see FIG. 7) and the electrode 96 (see FIG. 7) provides greater sensitivity to one analyte (e.g. NO) and discriminates against another analyte (e.g. CO). In other words, the distance between the electrode 90 and the electrode 96 provides an optimal sensitivity to NO, while discriminating against CO.

With the above explanations in mind, sensor devices (and corresponding sensor systems) of the present disclosure are effective in sensing the presence and concentration of NO, including discriminating against the presence of CO. The sensor devices include a sensing element of $WO_3$ and $Cr_2O_3$. The $WO_3$ and $Cr_2O_3$ can be formed adjacent (side-by-side) one another as described above. In other embodiments, the sensor devices of the present disclosure are a mixture of $WO_3$ and $Cr_2O_3$. As described below, non-limiting examples of NO sensor devices in accordance with principles of the present disclosure were constructed and subjected to testing to confirm viability in sensing NO, including sensing NO in human breath.

EXAMPLES

Non-limiting examples of NO sensor devices in accordance with principles of the present disclosure were constructed as follows. Chromium (III) oxide (99%) powder, tungsten (VI) oxide (99.8%) powder, alpha-terpineol (96%) and gold wires (0.127 mm dia, 99.99%) were obtained from Alfa Aesar (Ward Hill, Mass., USA). A dutlet substrate (17.5 mm×4.5 mm) was obtained from FormFactor Inc. (USA). It is made of polymer (maximum heating temperature at 350° C.) with gold microspring arrays. All test gases (described below) including $N_2$, $O_2$ and NO were obtained from Praxair (Danbury, Conn., USA)

Material Properties

Figure 12A:
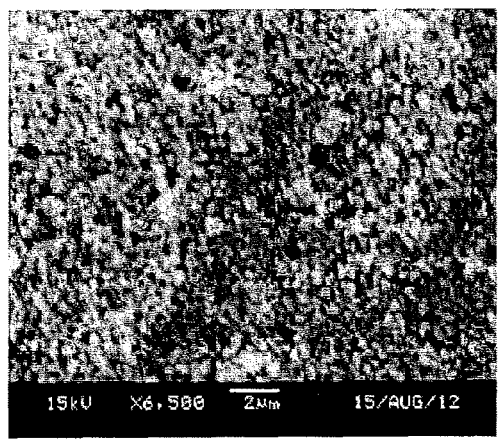
FIG. 12A is an SEM micrograph of a $Cr_2O_3$ film after heating at 300° C. for 10 hours and useful with sensor devices of the present disclosure.
Figure 12B:
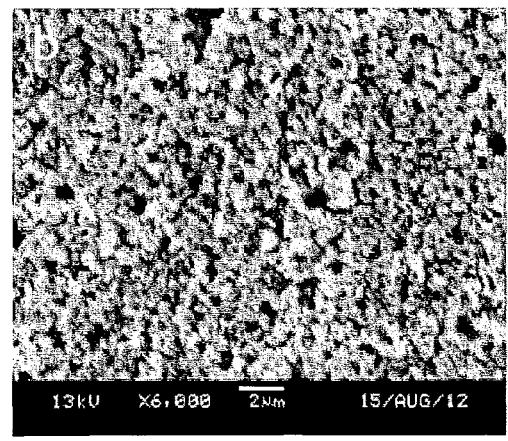
FIG. 12B is an SEM micrograph of a $WO_3$ film after heating at 300° C. for 10 hours and useful with sensor devices of the present disclosure

Various properties of the $Cr_2O_3$ and $WO_3$ materials were obtained. For example, FIG. 12A is an SEM micrograph (JEOL JSM-5500 scanning electron microscope) of the heated $Cr_2O_3$ powder (300° C. for 10 hours), and FIG. 12B is an SEM of the heated $WO_3$ powder. The micrographs show that the particles sizes are <200 nm in both cases.

Figure 13A:
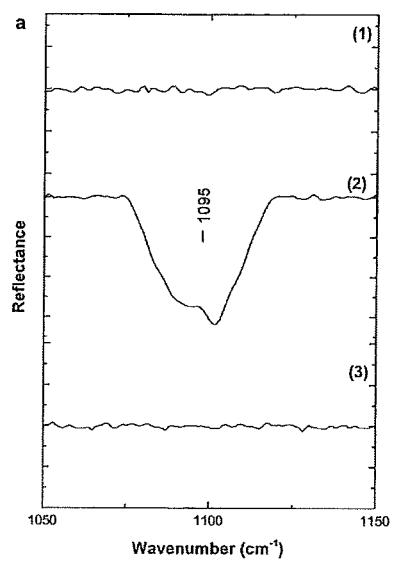
FIG. 13A is an IR spectra of a $WO_3$ powder and useful with sensor devices of the present disclosure.

In-situ diffuse reflectance infrared studies (Perkin Elmer 400) were also performed and involved heating the metal oxide in air to 500° C., and cooling to room temperature and obtaining an IR spectrum. Then the oxide was heated to 300° C., exposed to NO, cooled to room temperature in presence of NO, and the spectrum recorded. This was followed by reheating the sample to 500° C. in air and cooling to room temperature and rerecording the spectrum. FIG. 13A shows the data for $WO_3$; the only reproducible change (2-3 independent measurements) was observed upon exposure to NO was in the 1050-1150 $cm^{-1}$ region. A band appears at 1095 cm upon NO exposure and disappears with heating in air. Assignment of this peak to $NO^-$ was made by comparison with literature. In the case of MgO and $CeO_2$, a strong band has been reported at 1160 and 1171 $cm^{-1}$, respectively and assigned to $NO^-$ species. These are also weaker bands at ~1250 and ~850 $cm^{-1}$ that is also reported, but were not observed. Along with $NO^-$ on MgO, $CeO_2$, bands due to $NO_2^-$ and $N_2O_2^{2-}$ were also reported.

Figure 13B:
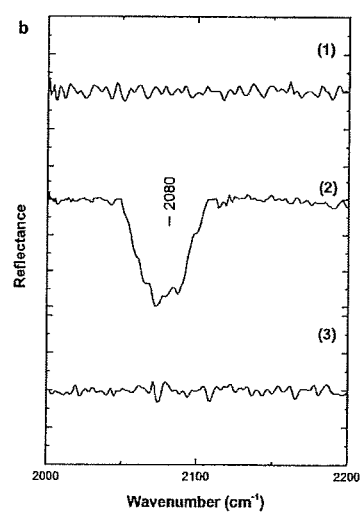
FIG. 13B is an IR spectra of a $Cr_2O_3$ powder and useful with sensor devices of the present disclosure.

The infrared experiment was repeated with $Cr_2O_3$ with 1000 ppm NO, but no spectroscopic changes were observed. The experiment was repeated with 50% $NO/N_2$, and a band at 2080 $cm^{-1}$ was reproducibly observed, this band disappeared on heating, and this data is shown in FIG. 13B. The band at 2080 $cm^{-1}$ was assigned to $NO^+$, based on reports in the literature. There is a report of NO adsorption on reduced chromia, and prominent bands at 1735 and 1865 $cm^{-1}$ were reported, and assigned to a $N_2O_2$ dimer. With chromia on alumina, a band at 2260 $cm^{-1}$ was assigned to $NO^+$. Adsorption of NO on zeolites led to a broad band at 2160 $cm^{-1}$ (with a shoulder at 2215 $cm^{-1}$), and assigned to $NO^+$.

Figure 14A:
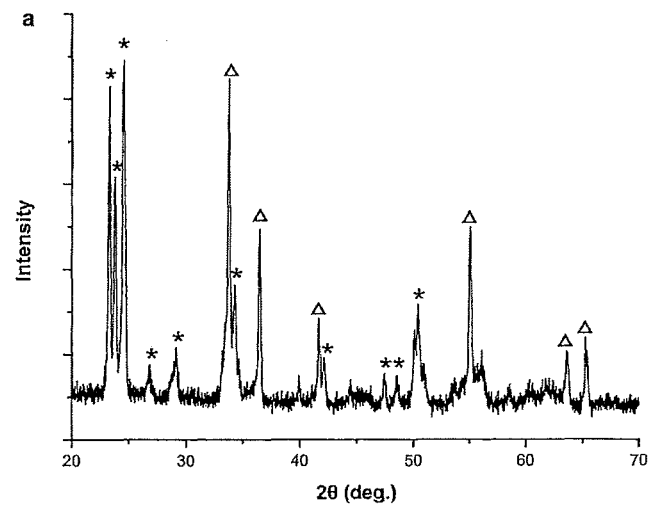
FIG. 14A is graph illustrating XRD patterns of a mixture of $WO_3$ and $Cr_2O_3$ powders and useful with sensor devices of the present disclosure.
Figure 14B:
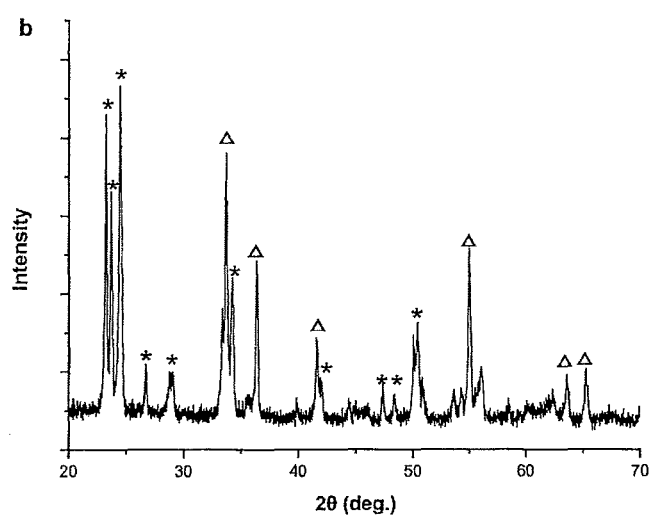
FIG. 14B is a graph illustrating XRD patterns of the mixture plotted in FIG. 14A and after heating at 500° C. for 3 hours.

FIGS. 14A and 14B show an x-ray diffraction (XRD) of a mixture of $WO_3/Cr_2O_3$ at room temperature (FIG. 14A) and after heating at 500° C. (FIG. 14B). $WO_3$ peaks are indicated with asterisks (*), $Cr_2O_3$ peaks are indicated with triangles (Δ). All the peaks observed after thermal treatment can be assigned to $WO_3$ and $Cr_2O_3$, indicating that there is no chemical reaction between these oxides up to temperatures of ~500° C. XRD analysis was carried out on a Rigaku Geigerflex X-Ray powder diffractometer using Cu-Kα radiation.

Mixed Powder Sensor Device Construction

Two types of non-limiting example sensor devices were constructed and examined: a mixture of powders, and powders adjacent to each other. For powder mixtures, mixtures of $WO_3$ and $Cr_2O_3$ in weight ratios varying from 1:1 to 11:1 were prepared and applied to alumina substrates of 15 mm×10 mm with interdigitated gold lines of 0.25 mm spacing (obtained from Case Western Reserve University Electronics Design Center). Gold lead wires (Alfa Aesar) were connected with gold paste from Heraeus. The devices were heated at 600° C. for 2 h in order to remove organic binders from the gold paste. The powders of $Cr_2O_3$ (Aesar), and $WO_3$ (Alfa Aesar) were suspended in alpha-terpineol and sonicated for 10 min. The suspensions were drop casted onto the interdigitated gold electrodes and dried at 300° C. for 10 hr.

Adjacent Sensor Device Construction

Dutlets were used to form exemplary sensor devices with adjacent placement of powders. $WO_3$ or $Cr_2O_3$ powder was ground thoroughly and then mixed with alpha-terpineol to form a paste, which was then painted on either side of the substrate surface and calcined in a tube furnace (Lindberg/Blue) at 300° C. for 12 h. Before testing, all samples were exposed to flowing $N_2$ at 300° C. overnight.

Figure 15A:
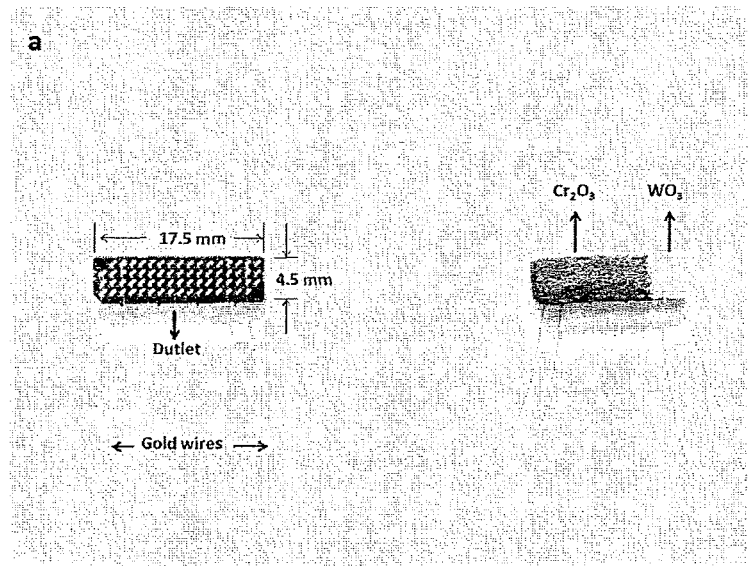
FIG. 15A is a photograph of components of a sensor device in accordance with principles of the present disclosure including a dutlet substrate and a sensing element comprising $Cr_2O_3$ and $WO_3$.

FIG. 15A shows the substrate, a plastic device (left of figure) on which $WO_3$ and $Cr_2O_3$ were deposited and in contact at a common interface (right of figure). The substrate was designed in such a fashion that resistances across different lengths of $WO_3$ and $Cr_2O_3$ could be measured (via the Au wires shown in the Figure).

Figure 15B:
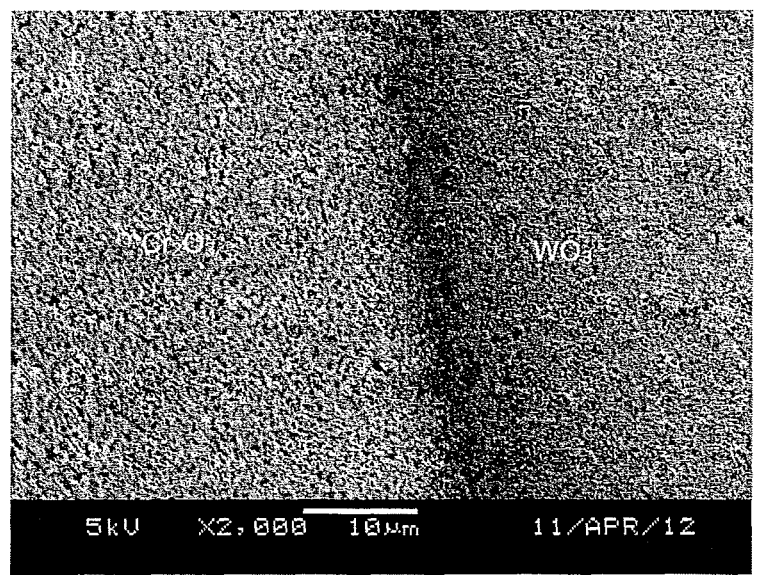
FIG. 15B is an SEM micrograph of a portion of the sensing element of FIG. 15A, including a junction of the $Cr_2O_3$ and $WO_3$ materials.
Figure 17:
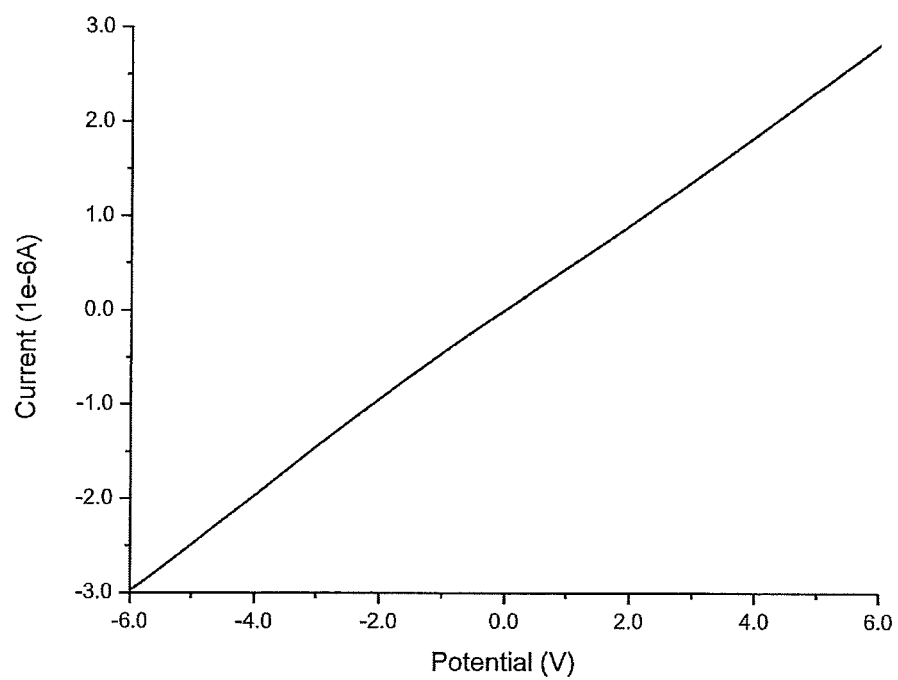
FIG. 17 is a graph illustrating measured potential-current values across a junction of Cr2O3 and WO3 materials in the presence of a 80% nitrogen/20% oxygen gas mixture.

FIG. 15B shows the SEM of the $WO_3$—$Cr_2O_3$ junction or interface, exhibiting intermixing of the two particles at the interface. A more detailed view of the intermixing is evident from Raman imaging studies (performed on a Renishaw-Smiths Detection Combined Raman—IR Microprobe with laser at 632.8 nm). As shown in FIGS. 16A and 16B, Raman spectra of $WO_3$ (FIG. 16A) and $Cr_2O_3$ (FIG. 16B) are quite distinct, with prominent bands for $WO_3$ at 273, 717 and 806 $cm^{-1}$ and relatively weak bands for $Cr_2O_3$ at 349, 551 and 609 $cm^{-1}$. In the Raman imaging study, spectra were collected along ~2 μm of the interface (proceeding from the $WO_3$ side to the $Cr_2O_3$ side) and the intensities in the regions 537-568 $cm^{-1}$ (indicative of $Cr_2O_3$) and 774-841 $cm^{-1}$ (indicative of $WO_3$) were computed. FIG. 16C shows a plot of the integrated intensities, the $WO_3$ signal is maximum at 0 μm and begins to decrease at ~500 μm and reaches zero counts at ~1500 μm and there is a symmetry in the increase in the $Cr_2O_3$ peaks. As a point of reference, in the graph of FIG. 16C, straight line with circle markers reflects the $WO_3$ signal between 774 to 841 $cm^{-1}$; a dashed line with square markers reflects the $Cr_2O_3$ signal between 537 to 568 $cm^{-1}$. Both lines are smoothed with a 6-order polynomial curve. These imaging studies indicate that the particles are intermingled over length scales of about a micron. The I-V curve measured across the $Cr_2O_3$—$WO_3$ interface in 20% $O_2$ balanced with $N_2$ at 300° C. is shown in FIG. 17. The current-voltage measurements were performed on a CHI760D electrochemical workstation (CH Instruments, Inc. USA) under a scan rate of 0.1 V/s from −6.0 to 6.0 V. The curves are linear, exhibiting an Ohm's law relationship, with no evidence of any rectification.

Sensor Device Testing

Gas sensing experiments were performed on the example NO sensor devices within a quartz tube placed inside a tube furnace (Lindberg/Blue) at 300° C., with a PC-controlled gas delivery system with calibrated mass flow controllers (Sierra Instruments Inc.). The test gas mixtures containing different concentrations of NO at constant oxygen content of 20 vol % were prepared by diluting NO with $O_2$ and $N_2$. The total flow rate was maintained at 200 $cm^3$/min. The resistance of the sensor device was recorded by an Agilent 34972A LXI data acquisition/switch unit or a HP34970A at a scan rate of 0.1 Hz. The accurate concentration of NO in the ppb range was independently performed by using pre-calibrated Sievers 280i nitric oxide analyzer (GE Electronics, Boulder, Colo., USA)

In addition to testing the example NO sensor devices in the presence of known gas mixtures, experiments were performed using exhaled human breath. Exhaled breath samples were collected in Mylar bags from volunteers. Typically, for healthy volunteers, the amount of NO is less than 10 ppb. Thus, to establish the capability of the sensor devices and sensor systems of the present disclosure, it was necessary to get higher concentrations of NO into the bag. This was done by introducing small amounts of bottled NO into the bag containing the human breath, and the exact level of NO in the bag was measured using the Sievers 280i Nitric Oxide Analyzer (GE Electronics, Boulder, Colo.). The concentration ranges examined were between 67 and 290 ppb NO. The Mylar bags were reused and thoroughly cleaned before each use with flowing nitrogen (99.998% purity) gas. Instead of mass flow controllers, a pump (Hargraves Technology Corporation, Mooresville, N.C.) was used to maintain a constant flow rate of 200 $cm^3$/min. In the experimental setup, the breath sample and the ambient air were bubbled through water at room temperature. The inlet of the quartz tube was connected with a three way valve which allows either breath sample or ambient air.

Gas Testing Results—Mixed Powders

Figure 18:
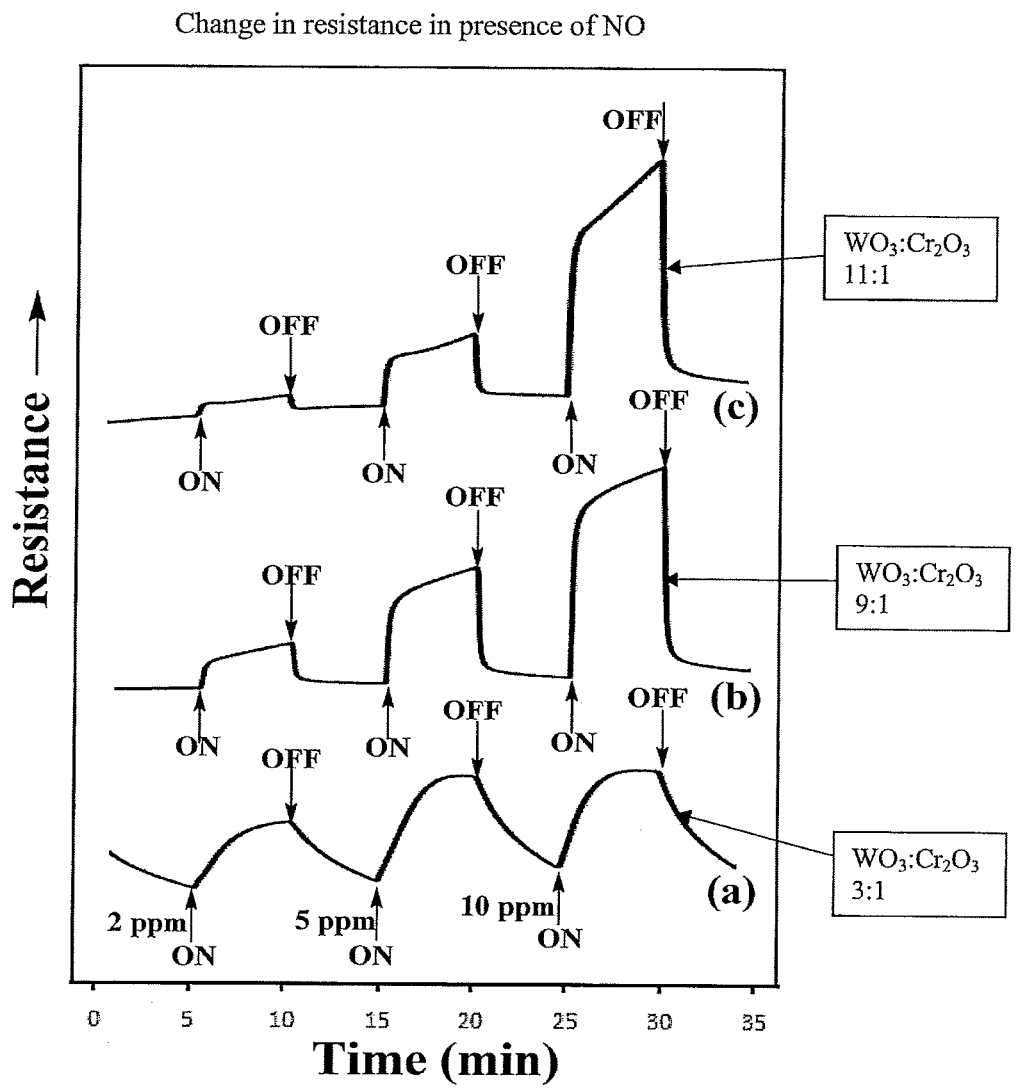
FIG. 18 is a graph illustrating measured resistance of different mixtures of $WO_3:Cr_2O_3$ in the presence of various gases containing NO.
Figure 19:
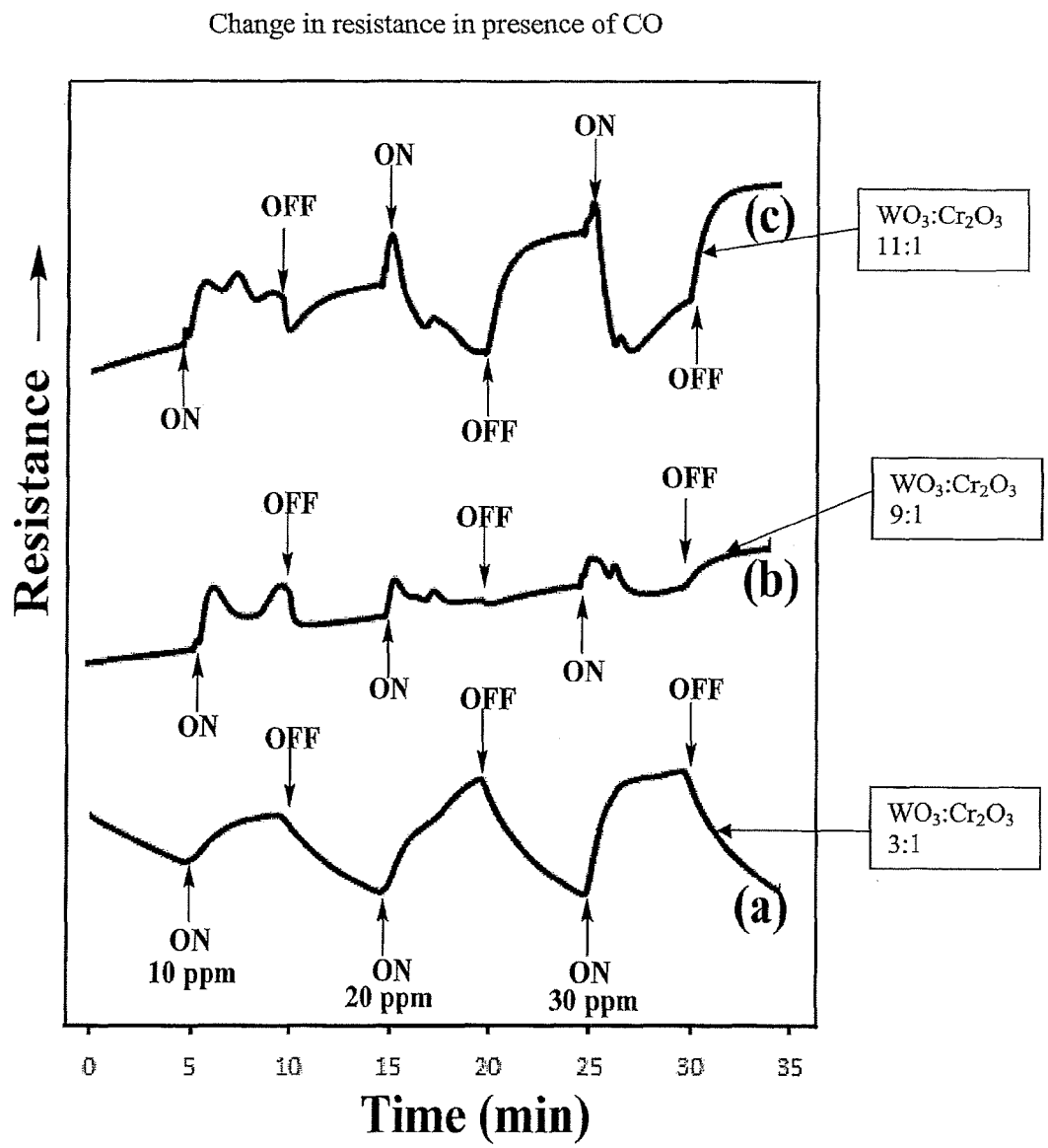
FIG. 19 is a graph illustrating measured resistance of different mixtures of $WO_3:Cr_2O_3$ in the presence of various gases containing CO.

Example sensor devices comprising mixtures of $WO_3$ and $Cr_2O_3$ in weight ratios varying from 1:1 to 11:1 were prepared as described above, and the resistance changes with NO (2, 5, 10 ppm) and CO (10, 20, 30 ppm) in a background of 20% oxygen (remainder $N_2$) was examined at 300° C. The data for three of these mixtures with weight/weight ratios of $WO_3$ and $Cr_2O_3$ of 3:1, 9:1 and 11:1 are shown in FIGS. 18 and 19. For NO (FIG. 18), with all the powder mixtures, the resistance exhibited an increase. For CO (FIG. 19), however the resistance exhibited an increase with 3:1 $WO_3$:$Cr_2O_3$ ratio, a diminished signal (almost no change in resistance at ~20 ppm CO) for the 9:1 ratio, and a decrease in resistance (clearly for 20 and 30 ppm CO) for the 11:1 ratio.

Gas Testing Results—Adjacent Powders

Figure 20A:
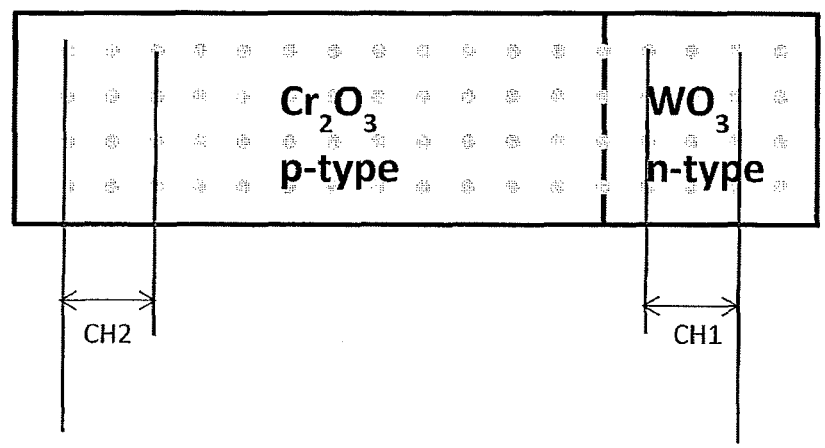
FIG. 20A is a schematic illustration of a sensor device in accordance with principles of the present disclosure and indicating a conductivity measuring protocol.
Figure 20B:
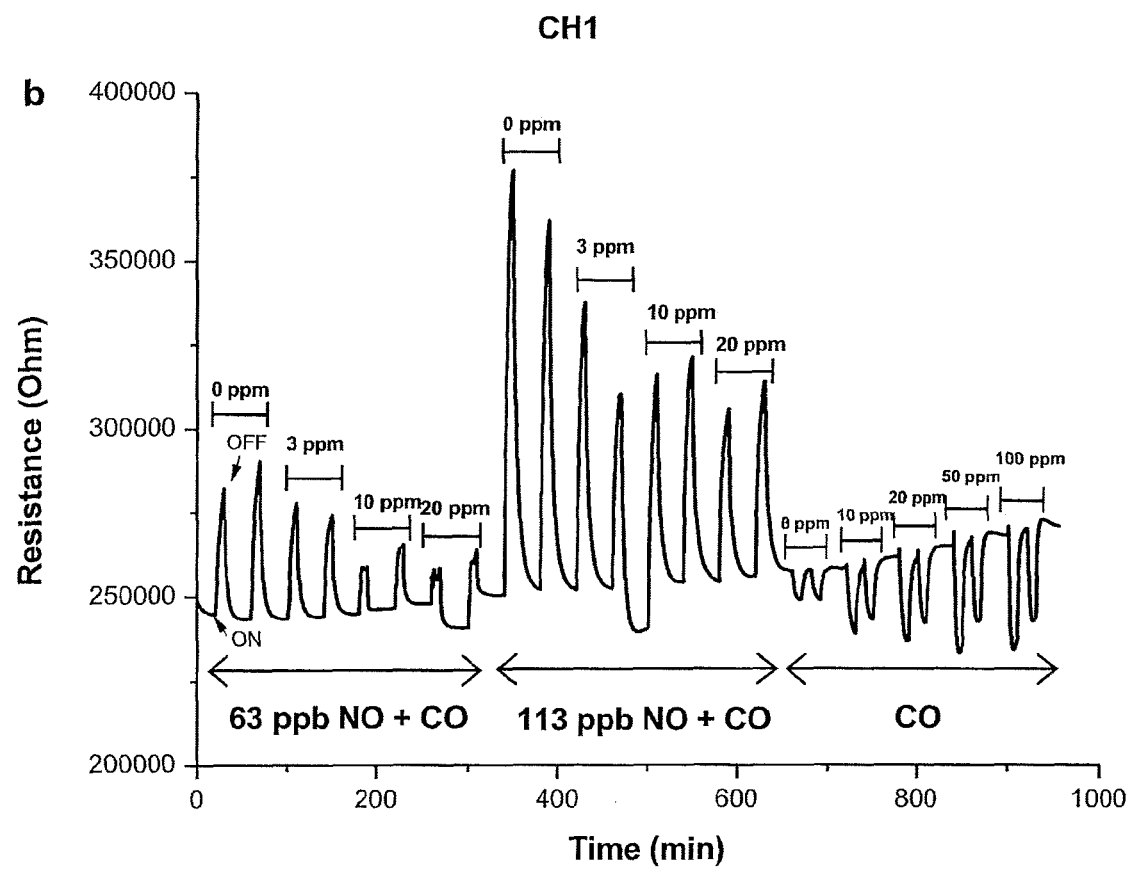
FIGS. 20B and 20C are graphs illustrating measured resistances at the channels indicated in FIG. 20A.
Figure 20C:
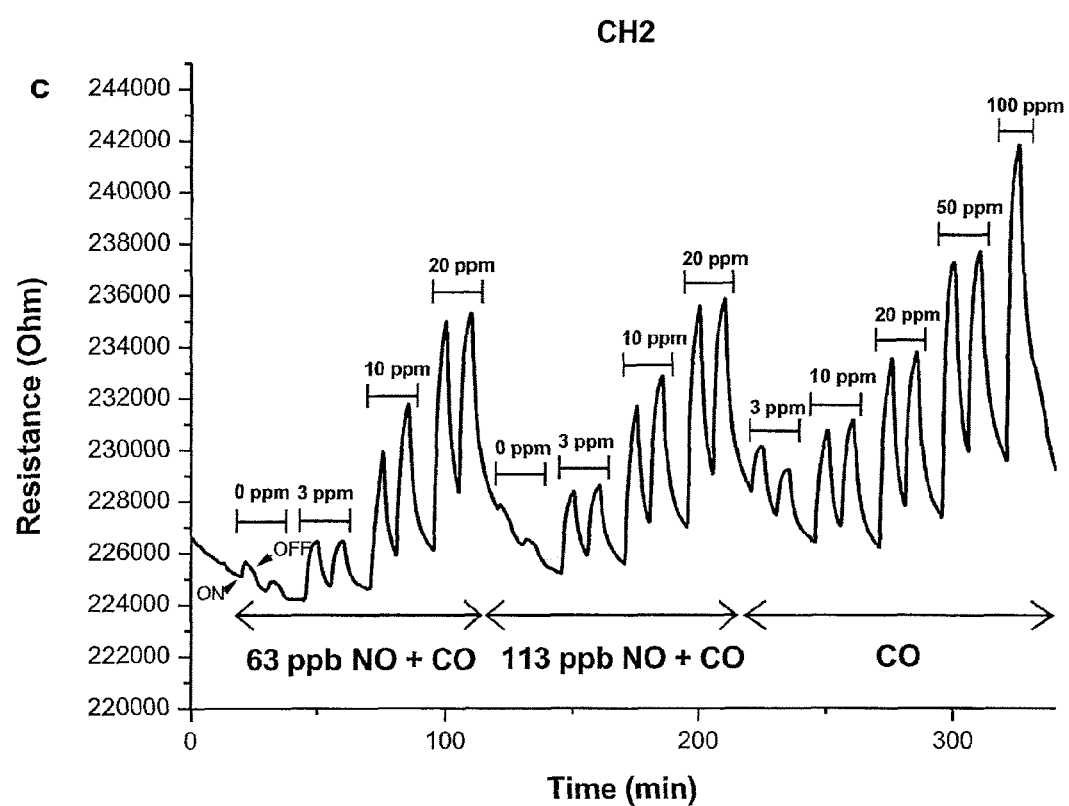

Testing of the example sensor devices incorporating $Cr_2O_3$ adjacent $WO_3$ included first measuring resistances within just the $Cr_2O_3$ region and within just the $WO_3$. FIG. 20A shows a schematic of the sensor device and corresponding testing scenario. FIGS. 20B and 20C show the resistance changes for gas mixtures of 63 ppb and 113 ppb NO with varying quantities of CO (0, 3, 10, 20 ppm) and CO alone (3, 10, 20, 50 and 100 ppm) at 200 $cm^3$/min flow rate and 300° C.

In case of channel 1 ("CH1") resistance across $WO_3$ is measured, and for CO alone, there is a decrease in resistance, as shown in FIG. 20B (with FIG. 20B plotting typical measured resistance response curves). For NO alone (63, 113 ppb), there was an increase in resistance for CH1. With mixtures of NO and CO, the resistance change in the presence of NO becomes increasingly smaller, indicating that there is a significant interference being caused by CO.

Resistance measurements made across Channel 2 ("CH2"), which is primarily due to $Cr_2O_3$ (FIG. 20A), are shown in FIG. 20C (with FIG. 20C plotting typical measured resistance response curves). For CO alone, there is an increase in resistance. For NO alone, there is a slight increase in resistance. For the mixture of gases, the resistance seems dominated by CO, thus suggesting strong interference towards NO signal.

The resistance changes across the $Cr_2O_3$—$WO_3$ boundary with different lengths of each metal oxide included was also examined. A schematic representation of the sensor device and testing protocol is provided in FIG. 21A. Resistance changes for gas mixtures of 63 ppb and 113 ppb NO with varying quantities of CO (0, 3, 10, 20 ppm) and CO alone (3, 10, 20, 50 and 100 ppm) at 200 $cm^3$/min flow rate and 300° C. were recorded at various distances between the two oxides (i.e., Channel 3 ("CH3")). FIG. 21B plots a typical resistance response curve of CH3 and illustrates that with contributions from the two oxides, the interference of CO towards NO is largely eliminated. For CO alone, it is observed that the signal from 3-20 ppm ppm CO is also negated, with slight resistance increases for 50 and 100 ppm. Comparing the mixtures of NO and CO, it is clear that the interference from <20 ppm CO to NO is minimized. FIG. 21C shows the calibration curves to NO at concentrations <400 ppb, the signal being defined as $R/R_o$ where R and $R_o$ are resistances in the presence of NO (with 20% $O_2$, balance $N_2$) and $R_o$ due to the background gas (20% $O_2$, balance $N_2$).

Human Breath Testing Results

Figure 22:
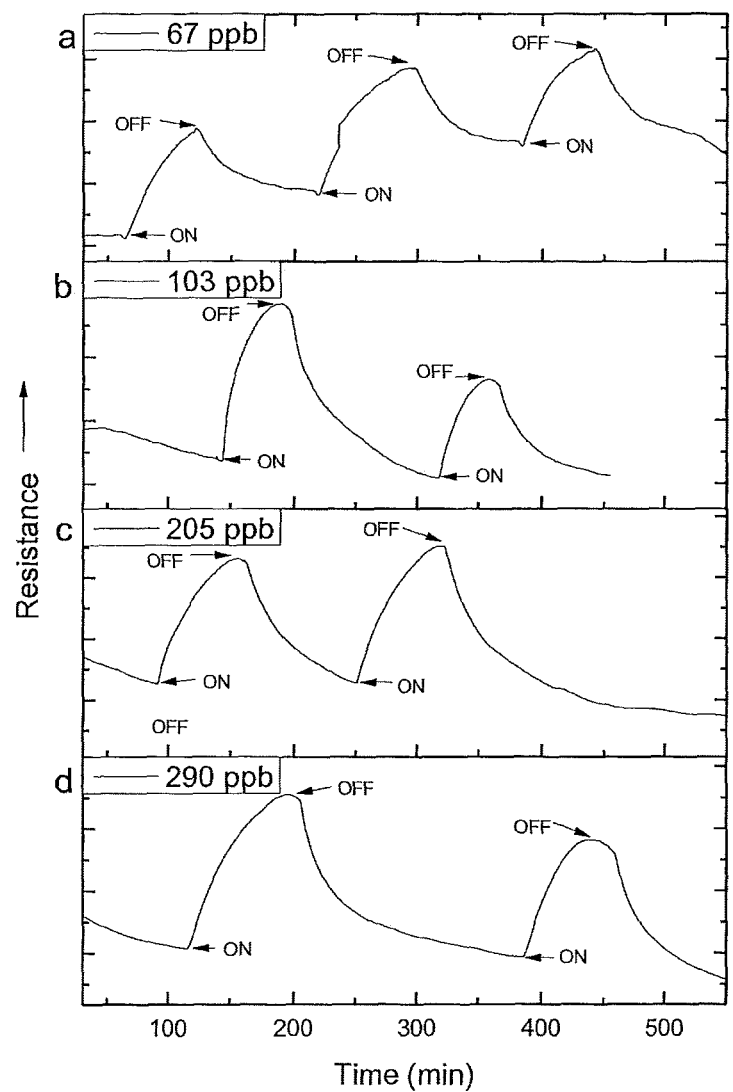
FIG. 22 is a graph illustrating measured resistances of the sensor device of FIG. 21A to human breath infused with varying amounts of NO.
Figure 23:
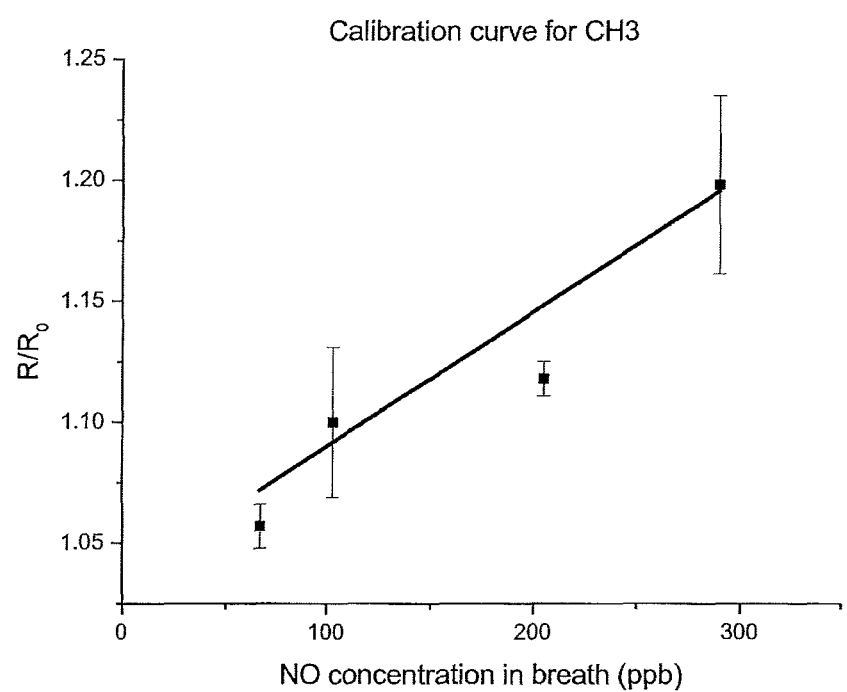
FIG. 23 is a calibration curve obtained from the data of FIG. 22.

Human breath samples were collected in Mylar bags and spiked with different concentrations of NO (67, 103, 205, 290 ppb), and concentration independently measured by a chemiluminescence analyzer. These gas mixtures were then passed over the p-n sensor device of FIG. 21A and the resistance changes corresponding to CH3 were measured. The sensor device was operated at 300° C. and a flow rate of 300 cm$^3$/min was employed. For the background, air bubbled through water was used. FIG. 22 plots the measured resistances for the different NO concentrations, with several repeat measurements. The response/recovery time for the signal was of the order of 60 min. FIG. 23 shows the calibration curve generated from these measurements.

Discussion of Results $WO_3$ is one of the most extensively studied n-type semiconducting metal oxides for gas sensing. The resistance decrease with CO (FIG. 20B) is explained by the following reaction $O_{ad}^- — WO_3 + CO$ (ad) $\rightarrow CO_2 + WO_3$ (e). $WO_3$ (e). With NO, an increase in resistance of the $WO_3$ film is observed, as has been reported previously. Based on the IR data shown in FIG. 13A, it is estimated that $NO^-$ is being formed on the $WO_3$ surface, and the increase in resistance is attributed to abstraction of electrons from the conduction band of the semiconductor.

$Cr_2O_3$ is a p-type semiconductor. In the case of CO, the film of $Cr_2O_3$ shows an increase of resistance, and has been reported previously. CO will react with chemisorbed oxygen forming $CO_2$ and release electrons that can trap the majority hole carriers and result in increase in resistance. More interesting is the observation with NO, which also exhibits an increase of resistance of the $Cr_2O_3$ film. This observation with NO has also been reported, though no explanations have been forthcoming. The infrared data (FIG. 13B) suggests that NO is acting as an electron donor forming $NO^+$ and possibly reducing $Cr^{4+}$ to $Cr^{3+}$. Such electron transfer will result in neutralizing holes in the conduction band, and increase in the resistance. Breakdown voltages of $Cr_2O_3$ in the presence of NO, $NO_2$ have been reported and used as a basis for sensing these gases, and the formation of $NO^+$ on $Cr_2O_3$ has also been proposed.

The XRD of the mixture of the powders of $Cr_2O_3$ and $WO_3$ heated to 500° C. indicate that there is no chemical reaction between these oxides. From the resistance changes to NO and CO of the mixture (FIGS. 18 and 19), several trends are evident. In the case of NO, for all mixtures ratios, there is an increase in resistance. However for CO, there is a trend of resistance increase at higher relative concentrations of $Cr_2O_3$ (3:1 $WO_3$:$Cr_2O_3$) and resistance decrease at higher concentrations of $WO_3$ (11:1 $WO_3$:$Cr_2O_3$) with the 9:1 $WO_3$:$Cr_2O_3$ mixture exhibiting minimal resistance change (e.g. 20 ppm CO almost remains at baseline resistance). Two observations are relevant to these characteristics. First, it is difficult to reproduce the exact ratio of powders at which the cancellation takes place, though the trends indicated above are always observed. Second, the cancellation in signal appears for only a certain concentration of CO (e.g., with the 9:1 ratios, 10 ppm and 30 ppm CO provide resistance increases and decreases, respectively, while there is an almost null response to 20 ppm CO).

The irreproducibility with mixing the powders arises from the size and density differences of the particles and different settling dynamics once the ink is deposited on the interdigitated alumina substrate. Also, the exact layer from which the sensing occurs is debated, with the likelihood that it is the layer closest to the electrodes, and so the settling of the particles becomes critical in determining response.

The trend of resistance changes (from increasing to decreasing) with CO for mixtures of p- and n-type semiconducting oxides ($TiO_2$) has been reported in the literature. Several explanations have been suggested, including percolation paths for p and n type that interfere with each other resulting in cancellation. With p-type $Co_3O_4$ on n-type ZnO, as the thickness of the p-type layer increased, sensitivity towards both oxidizing and reducing gases decreased. This was attributed to lack of porosity, but could be also due to the electrical cancellation effect from the p- and n-type material. Our observation that with the $Cr_2O_3/WO_3$ mixture, the presence of NO always leads to an increase in resistance is consistent with the results from individual powders exposed to NO.

The results with mixtures of powders above clearly demonstrate that it is possible to use the p-n cancellation with the oxidizing gas (CO) to generate a selective sensor to NO. However, the issues with reproducibility in the powder preparation and deposition and the fact that cancellation at a particular powder mixture only occurs for a particular concentration of CO may make this impractical. Placing the powders adjacent to each other and including different lengths of the powders in making resistance measurements parallels the concept of making powders of different ratios, but the experimental design is considerably simplified, since only one sample is required and from which obtaining multiple sensor measurements are obtained.

There are several studies in the literature that have explored adjacent p-n materials, but the focus has been on creating rectifying devices. As seen from the I-V measurements, we did not observe any rectification. This is consistent with literature, where it has been observed that rectification is only observed if two sintered metal oxides are joined to each other. In a study of ZnO/CuO contact ceramics prepared by presenting the two pellets against each other, it was noted that ZnO pellet sintered at 900° C. produced a linear I-V characteristic, whereas ZnO pellet sintered at 1100° C. exhibited characteristics of a p-n diode (CuO sintered in both cases at 880 and 895° C.). Clearly, the nature of the interface determined I-V curve. It was concluded that that in the more poorly sintered sample, leakage current was dominant. The Raman imaging studies show that the interface is about ~1000 μm where the $WO_3$ and $Cr_2O_3$ are intermixed, and reminiscent of a poorly sintered sample.

Figure 21A:
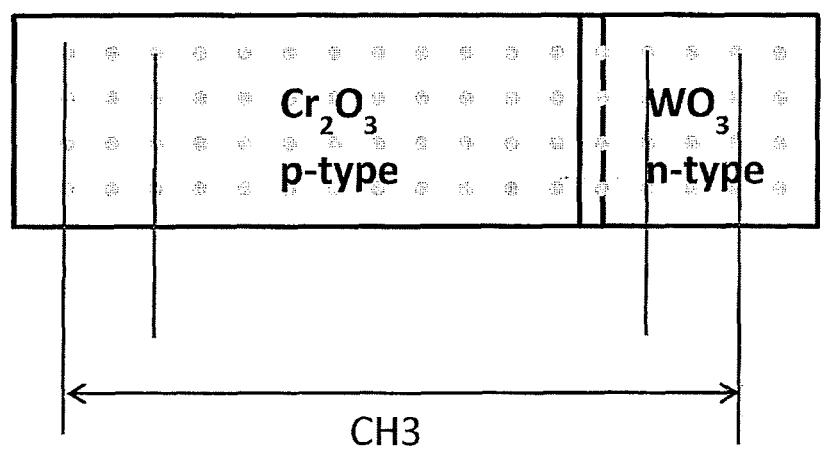
FIG. 21A is a schematic illustration of a sensor device in accordance with principles of the present disclosure and indicating a conductivity measuring protocol.
Figure 21B:
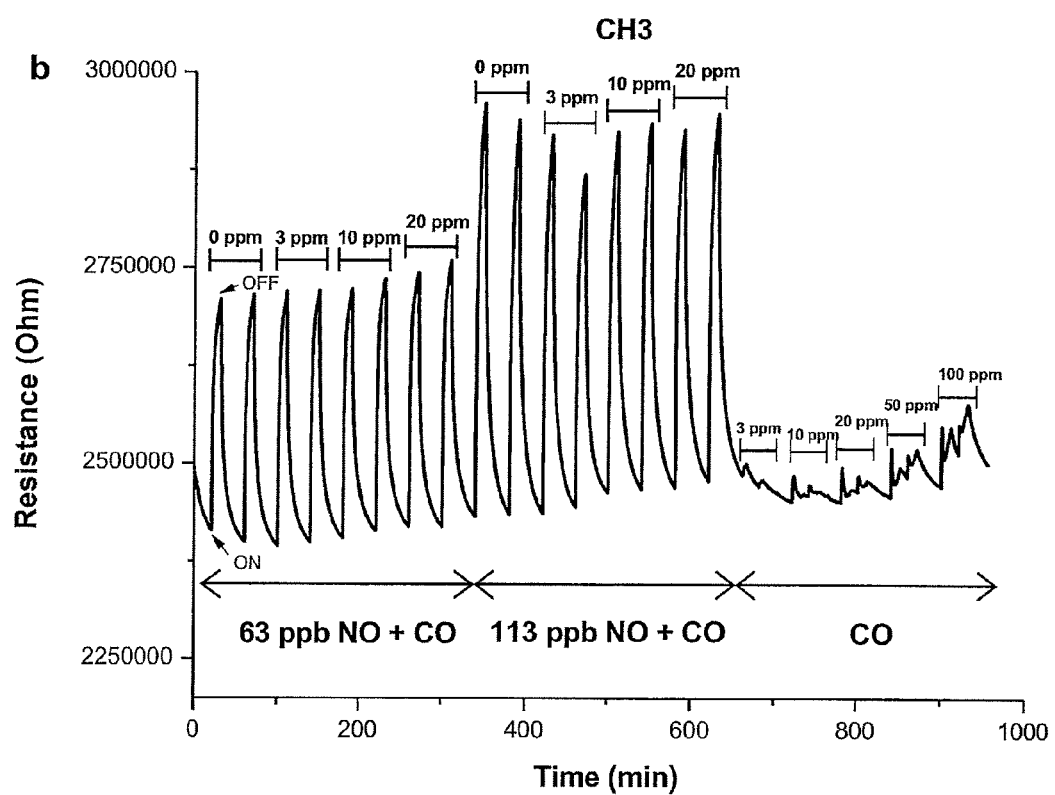
FIG. 21B is a graph illustrating measured resistances at the channel indicated in FIG. 21A.
Figure 21C:
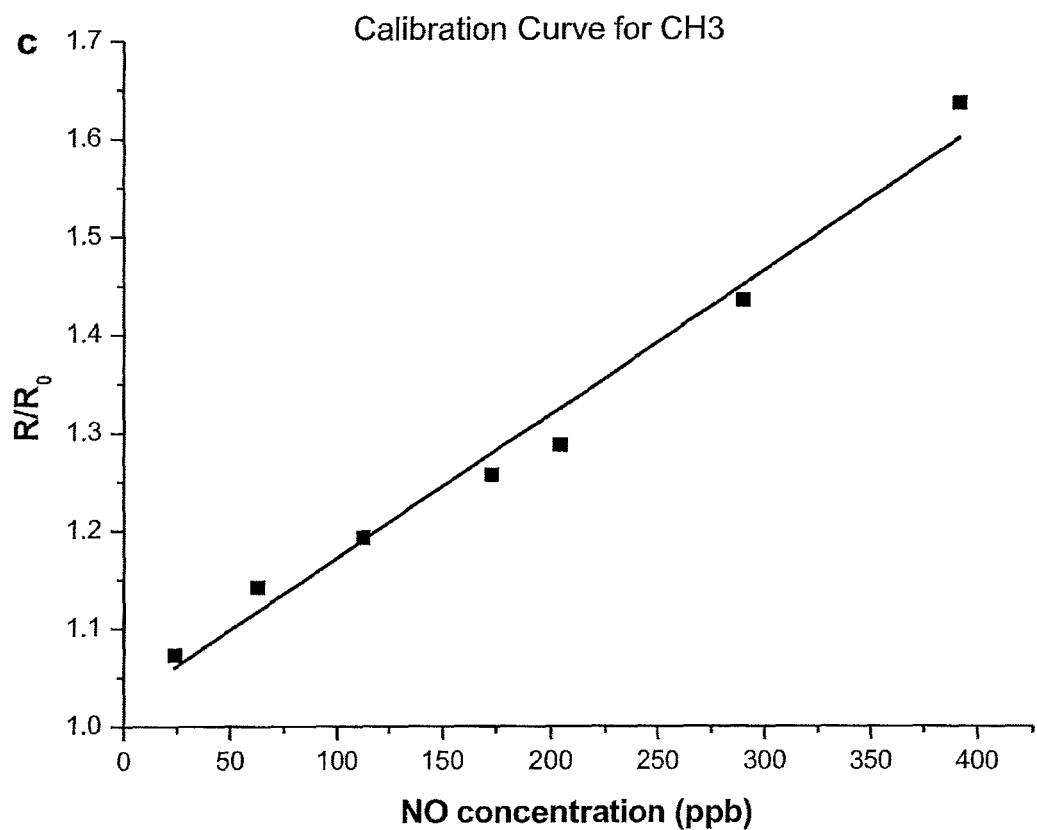
FIG. 21C is a calibration curve obtained from the data of FIG. 21B.

With the sensor devices of the present disclosure, the response to CO and NO can be continuously varied by choosing to include different fractions of the metal oxide, as shown in FIGS. 20A and 21A. For a particular choice (CH3), a sensor can be designed that is selective to NO (ppb) and discriminates against CO that is present at significantly higher concentrations (ppm). The calibration curves obtained with NO demonstrate that sensitivities in the tens of ppb are readily attained. Another advantage of the design is that there is a broad range of CO concentrations over which cancellation takes place (0-20 ppm) as compared to the powder mixtures.

For a practical demonstration of this device, spiked NO in human breath samples was measured. There are hundreds of other molecules in breath, and the humidity is almost 100%. So, the background used was humidified air. The data shown in FIG. 23 indicates that the sensor is responding to NO in human breath, though the response and recovery times are slow. Also, the magnitude of the signal is lower than that measured in dry air (FIG. 22C).

In conclusion, it was surprisingly found that a novel arrangement of p- and n-type metal oxides can lead to selective gas sensing of NO. The choice of NO as the sensing gas may be critical, because it has structural and electrical features that allow it to both accept and donate electrons, and therefore the signal on both the n- and p-type material provide an additive effect. If this device is used for sensing CO, it would always lead to reduced signals. Though it is likely that for different reducing gases (CO vs. $C_2H_5OH$), the cancellation of signals will occur with different contributions from the two oxides (experimentally manifested in canceled resistance observed at different lengths for different reducing gases), providing an opportunity for selectivity, but with reduced sensitivities.

Although the present invention has been described with reference to preferred embodiments, workers skilled in the art will recognize that changes can be made in form and detail without departing from the spirit and scope of the present invention.

What is claimed is:

1. A sensor device for sensing NO, the sensor device comprising:
    a sensing element including:
        a first region consisting of $WO_3$;
        a second region consisting of $Cr_2O_3$;
        at least a first electrode established within the first region;
        at least a second electrode established within the second region; and
        wiring interconnecting the first and second electrodes;
    wherein the first region is adjacent to and contacts the second region; and
    wherein a measured resistance along the wiring is indicative of the presence of NO in a gas interlacing with the sensing element.

2. The sensor device of claim 1, further comprising:
    a platform assembly maintaining the first and second electrodes as part of an electrode lead array selectively contacting the sensing element.

3. The sensor device of claim 2, wherein the platform assembly is configured to selectively alter a location of contact of the first electrode within the first region and selectively alter a location of contact of the second electrode within the second region.

4. The sensor device of claim 2, wherein the platform assembly is further configured to selectively alter a distance between the first and second electrodes.

5. The sensor device of claim 1, wherein a location of the first electrode relative to the first region and a location of the second electrode relative to the second region are selected such that the measured resistance is unaffected by the presence of CO in a gas sample interfacing with the sensing element.

6. The sensor device of claim 1, wherein the sensing element defines a length from a first side to an opposing second side, the first side being defined by an edge of the first region opposite the second region, the second side being defined by an edge of the second region opposite the first region, and further wherein a location of the first electrode relative to the first region and a location of the second electrode relative to the second region are selected such that the wiring encompasses a combined amount of the $WO_3$ material and the $Cr_2O_3$ material in the length direction that is pre-determined to generate a measured resistance indicative of the presence of NO in a gas sample interfacing with the sensing element.

7. The sensor device of claim 6, wherein the pre-determined combined amount is selected such that the measured resistance is unaffected by the presence of CO in the gas sample interfacing with the sensing element.

8. The sensor device of claim 1, further comprising:
    a third electrode established within the first region at a location separate from the first electrode;
    a fourth electrode established with the second region at a location separate from the second electrode; and
    wiring interconnecting the third and fourth electrodes;
    wherein a measured resistance along the wiring interconnecting the third and fourth electrodes in comparison with the measured resistance along the wiring interconnecting the first and second electrodes is indicative of a concentration of NO in a gas interfacing with the sensing element.

9. The sensor device of claim 1, wherein the $WO_3$ contacts the $Cr_2O_3$ at a diffuse p-n junction formed at an interface between the first and second regions.

10. A sensor system for sensing NO in a gas sample, the system comprising:
    a sensor device having:
        a sensing element including:
            a first region consisting of $WO_3$;
            a second region consisting of $Cr_2O_3$;
            wherein the first region is adjacent to and contacts the second region,
            a first electrode established within the first region;
            a second electrode established within the second region; and
        a database correlating measured resistance along wiring between the first and second electrodes with presence of NO in a gas sample interfacing with the sensing element.

11. The system of claim 10, wherein the database further correlates an estimate of a concentration of NO in the gas sample based upon the measured resistance.

12. The system of claim 11, wherein a location of the first electrode relative to the first region and a location of the second electrode relative to the second region is selected such that the measured resistance is unaffected by the presence of CO.

13. The system of claim 10, wherein the database is a calibration curve.

14. The system of claim 10, further comprising a controller maintaining the database and electronically associated with the wiring.

15. The system of claim 14, wherein the controller is further programmed to:
    receive a plurality of measured resistance values generated by the sensor device in the presence of the gas sample; and
    estimate a concentration of NO in the gas sample based upon the plurality or measured resistances.

16. The system of claim 15, wherein a first one of the plurality of measured resistances corresponds to a first distance between corresponding electrodes in the first and second regions, respectively, and a second one of the plurality of measured resistances corresponds to a second distance between corresponding electrodes in the first and second regions, respectively, the first distance being different from the second distance.

17. The system of claim 10, wherein the system is configured to estimate the concentration of NO in human breath.

* * * * *